United States Patent
Lyon

(10) Patent No.: US 12,005,025 B2
(45) Date of Patent: Jun. 11, 2024

(54) SYSTEM AND METHOD OF APPLIED CONTRASTING THERAPY TO PELVIC REGIONS AND HUMAN DISTAL ANATOMY

(71) Applicant: Zachary Wood Lyon, Lewisville, NC (US)

(72) Inventor: Zachary Wood Lyon, Lewisville, NC (US)

(*) Notice: Subject to any disclaimer, the term of this patent is extended or adjusted under 35 U.S.C. 154(b) by 145 days.

(21) Appl. No.: 17/170,327

(22) Filed: Feb. 8, 2021

(65) Prior Publication Data

US 2022/0249318 A1 Aug. 11, 2022

(51) Int. Cl.
*A61H 9/00* (2006.01)
*A61H 23/02* (2006.01)
*A61N 5/06* (2006.01)

(52) U.S. Cl.
CPC ........... *A61H 9/0092* (2013.01); *A61H 23/02* (2013.01); *A61H 2201/0207* (2013.01);
(Continued)

(58) Field of Classification Search
CPC .......... A61H 9/0092; A61H 2201/0207; A61H 2201/0214; A61H 2201/0242;
(Continued)

(56) References Cited

U.S. PATENT DOCUMENTS 2,047,316 A * 7/1936 Erickson ............ A61H 23/0254
601/16
4,497,313 A * 2/1985 Kurosawa ............ A61H 35/006
601/78
(Continued)

FOREIGN PATENT DOCUMENTS

CN 105962436 A * 9/2016
CN 111135041 A * 5/2020 ............... A61F 7/00
(Continued)

OTHER PUBLICATIONS

Machine translation of description and claims for CN-112168468-A via espacenet (Year: 2021).*
(Continued)

*Primary Examiner* — Michael R Reid
*Assistant Examiner* — Tyler A Raubenstraw

(57) ABSTRACT

A system and method for providing Thermal contrast therapy are presented. The system may comprise a fluid membrane barrier, a human interface device (HID), fluid tubing, a pump, and a reservoir. The system may be operable to apply any combination of heat, cold, and pressurized compression, light energy, acoustic energy, and vibratory energy to a therapy recipient for treating anal-prostate-perineal and vaginal areas, as well as podological and other extremities. The system may be operable to impart a desired therapy temperature to the human interface device and to expand a membrane containing a therapy fluid. The expanded membrane may conform to the contours of a therapy site. Operation of the human interface device may be controlled using a remote-control device. The therapy recipient may be able to control the temperature of the fluid or gel, as well as reception of light energy, acoustic energy and vibratory pulsing energy to assist in treatment of one or more conditions.

18 Claims, 16 Drawing Sheets

(52) U.S. Cl.
CPC .............. *A61H 2201/0214* (2013.01); *A61H 2201/0242* (2013.01); *A61H 2201/105* (2013.01); *A61H 2201/1633* (2013.01); *A61H 2201/1635* (2013.01); *A61H 2201/164* (2013.01); *A61H 2201/165* (2013.01); *A61H 2201/5007* (2013.01); *A61H 2201/5082* (2013.01); *A61H 2201/5097* (2013.01); *A61H 2205/085* (2013.01); *A61H 2205/12* (2013.01); *A61H 2230/201* (2013.01); *A61N 5/0616* (2013.01)

(58) Field of Classification Search
CPC ...... A61H 2201/1635; A61H 2201/164; A61H 2201/165; A61H 2201/5007; A61H 2201/5082; A61H 2201/5097; A61H 2205/085; A61H 2205/12; A61H 35/006; A61H 2201/105; A61H 35/00; A61H 2009/0042; A61H 2201/1633; A61H 2230/201; A61H 9/0021; A61H 2201/02; A61H 2205/087; A61N 5/0616; A61F 7/00; A61F 2007/0028; A61F 2007/0048; A61F 2007/005
See application file for complete search history.

(56) References Cited

U.S. PATENT DOCUMENTS

| | | | |
|---|---|---|---|
| 7,328,476 B1* | 2/2008 | Heidemeyer, Jr. ... | A61H 35/006 601/114 |
| 2001/0018565 A1* | 8/2001 | Branch ................ | A61F 5/012 602/5 |
| 2002/0088791 A1* | 7/2002 | Yang ................... | A61K 8/92 219/439 |
| 2003/0226201 A1* | 12/2003 | Leung ................. | A61H 35/006 4/622 |
| 2004/0039430 A1* | 2/2004 | Gonzales ............. | A61F 7/123 607/105 |
| 2005/0126578 A1* | 6/2005 | Garrison .............. | A61H 9/0078 128/874 |
| 2005/0159690 A1* | 7/2005 | Barak .................. | A61H 9/0078 601/149 |
| 2005/0222651 A1* | 10/2005 | Jung ................... | A61F 7/02 607/104 |
| 2005/0235988 A1* | 10/2005 | Hansen ............... | F04B 35/06 128/200.24 |
| 2005/0277854 A1* | 12/2005 | Hatchett .............. | A61H 35/006 601/158 |
| 2006/0189905 A1* | 8/2006 | Eischen ............... | A61H 9/0085 601/151 |
| 2006/0207016 A1* | 9/2006 | Lev .................... | A61H 35/006 4/622 |
| 2006/0253967 A1* | 11/2006 | Wu ..................... | A61H 35/00 4/420.4 |
| 2007/0088235 A1* | 4/2007 | Tseng ................. | A61H 9/0078 601/151 |
| 2007/0131798 A1* | 6/2007 | Katsukawa .......... | A61H 33/005 239/455 |
| 2008/0021531 A1* | 1/2008 | Kane .................. | A61H 9/0078 607/111 |
| 2009/0069731 A1* | 3/2009 | Parish ................. | A61H 9/0078 601/150 |
| 2009/0177184 A1* | 7/2009 | Christensen ......... | A61H 9/0057 604/113 |
| 2010/0229884 A1* | 9/2010 | Alony ................. | A61H 7/004 15/210.1 |
| 2010/0324611 A1* | 12/2010 | Deming .............. | A43B 7/147 607/2 |
| 2011/0087143 A1* | 4/2011 | Bobey ................ | A61H 9/0078 601/152 |
| 2011/0238143 A1* | 9/2011 | Schock ............... | A61F 7/0053 607/104 |
| 2012/0065561 A1* | 3/2012 | Ballas ................ | A61H 9/0092 601/152 |
| 2012/0259394 A1* | 10/2012 | Knott ................. | A61F 7/0085 607/104 |
| 2013/0030331 A1* | 1/2013 | Quisenberry ........ | A61F 7/02 601/18 |
| 2013/0096490 A1* | 4/2013 | Pelkus ............... | A61M 35/00 604/24 |
| 2013/0211296 A1* | 8/2013 | Chau ................. | A61H 35/006 601/17 |
| 2013/0245519 A1* | 9/2013 | Edelman ............ | A61H 9/0078 601/152 |
| 2014/0018710 A1* | 1/2014 | Israel ................. | A61H 1/02 601/5 |
| 2014/0276257 A1* | 9/2014 | Santa Maria ........ | A61H 9/005 601/18 |
| 2014/0276288 A1* | 9/2014 | Randolph ........... | A61H 9/0057 601/152 |
| 2015/0182375 A1* | 7/2015 | Binversie ........... | A61F 7/007 601/18 |
| 2015/0305960 A1* | 10/2015 | Callahan ............ | A61H 9/0078 601/18 |
| 2016/0008206 A1* | 1/2016 | Devanaboyina ..... | A61H 23/02 601/136 |
| 2016/0051400 A1* | 2/2016 | Ruetenik ............ | A61F 7/103 601/15 |
| 2017/0209304 A1* | 7/2017 | Zumbrunnen ...... | A61F 7/0085 |
| 2017/0273851 A1* | 9/2017 | Larmer .............. | A61H 9/0092 |
| 2017/0304139 A1* | 10/2017 | Ross ................. | A61H 11/00 |
| 2018/0055721 A1* | 3/2018 | Quisenberry ....... | A61F 7/007 |
| 2019/0038446 A1* | 2/2019 | Takemoto .......... | A61F 7/10 |
| 2019/0104891 A1* | 4/2019 | Tran .................. | A61H 33/005 |
| 2019/0380865 A1* | 12/2019 | Baschnagel ........ | A61F 7/0085 |
| 2020/0147407 A1* | 5/2020 | Efremkin ........... | A61K 31/5375 |
| 2020/0170832 A1* | 6/2020 | Schaefer ............ | A61F 7/0053 |
| 2020/0289361 A1* | 9/2020 | Tian .................. | A61F 7/0085 |
| 2020/0390648 A1* | 12/2020 | Vo .................... | A61H 35/006 |
| 2021/0121355 A1* | 4/2021 | Behboodi .......... | A61H 1/0237 |

FOREIGN PATENT DOCUMENTS

| | | | | |
|---|---|---|---|---|
| CN | 112168468 A | * | 1/2021 | |
| KR | 20140134165 A | * | 5/2013 | ............. A61F 7/00 |
| WO | WO-03003989 A2 | * | 1/2003 | ............. A61H 35/00 |
| WO | WO-2014168624 A1 | * | 10/2014 | ............. A61D 9/00 |
| WO | WO-2017117305 A1 | * | 7/2017 | ............. A61B 5/0285 |
| WO | WO-2019073286 A1 | * | 4/2019 | |
| WO | WO-2020160823 A1 | * | 8/2020 | ......... A61H 33/0087 |

OTHER PUBLICATIONS

Machine translation of description and claims for CN-105962436-A via espacenet (Year: 2016).*
Machine translation of description and claims for CN-111135041-A via espacenet (Year: 2020).*
Machine translation of written description and claims for KR20140134165A via google patents (Year: 2014).*

* cited by examiner

Tubeaxial Type Fan

SYSTEM AND METHOD OF APPLIED CONTRASTING THERAPY TO PELVIC REGIONS AND HUMAN DISTAL ANATOMY

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

The subject matter herein relates generally to devices that are capable of providing heat and cooling contrast therapies to various regions of human anatomy.

For example, Hemorrhoids have plagued humans from time immemorial, particularly adult humans. Hemorrhoids are a livid and painful swelling formed by vein dilation in the anal cavity or rectum. Many treatments have been devised over the years, including chemical, thermal, electrical and surgical. Some involving elaborate treatment procedures and others somewhat drastic, and some of those already mentioned having possible damaging side effects. Many of the prior art techniques require administration by trained technicians or, in some cases, even physicians.

Hemorrhoids are simply blood-filled sacs or pads of normal anatomy in the anal canal. They may come and go and almost everyone has them at one time or another. They are very common in pregnancy and occur in two locations.

Those occurring above the internal sphincter are called internal hemorrhoids and those appearing outside the external sphincter are called external hemorrhoids.

Hemorrhoids cause itching, bleeding and pain. Internal hemorrhoids prolapse frequently through the sphincter and cause considerable discomfort. If the blood within them clots and becomes infected, they become painful and the risk of a thrombosis becomes present.

The primary complications of swollen hemorrhoids are bleeding, strangulation, and thrombosis. Trauma to the vein during defecation can cause enough bleeding to produce an iron deficiency anemia. Blood oozes or may even spurt out following a bowel movement.

Thrombosis, or clotting of the blood within the swollen hemorrhoid, can occur at any time and is manifested by debilitating and intense pain.

Prolapsed hemorrhoids may come out during defecation and spontaneously return. Prolapsed hemorrhoids may have to be repositioned by the patient or they may remain prolapsed.

A strangulated or hemorrhoid is a prolapsed hemorrhoid in which the blood supply is cut off by the anal sphincter. The blood within the prolapsed hemorrhoid becomes clotted and thrombosis occurs which is a very painful condition that brings extreme edema and inflammation.

The treatment methods range from warm baths through ointments and suppositories to surgery or injection chemotherapy to control the bleeding and to eliminate the varicose veins. Often several methods are combined to address various aspects of the disease.

Three treatments are commonly used for the treatment of swollen and thrombosing hemorrhoids are as follows: they are medical management, surgical excision, or laser surgery of the dilated veins and injection of a sclerosing substance into the tissues at the base of the vein. The injection of the sclerosing substance may be only temporarily effective.

Medical therapy, used only for small hemorrhoids with mild symptoms, includes reducing pressure by treating the constipation and thus keeping the stools soft. Pain is relieved with sitz baths, application of heat or cold, and astringent lotions, such as witch hazel. A recumbent position may be needed if the hemorrhoid is prolapsed or thrombosed.

Instead of the tube, some surgeons place pieces of Gelfoam or Oxycel gauze over the anal wounds. Dressings in such cases are held in place by a T-binder. The area is either left open to heal by granulation or sutured very painfully for the patient but has a high rate of success, whereas the sutured method, while far less painful, is more likely to cause infection and fails to heal well. The surgical excision and new laser surgery on a patient are usually repeated over and over again on a regular basis, which can become inconvenient.

The most frequent cause of hemorrhoidal swelling or thrombosing is straining at stools, which is most likely to happen when a person is constipated, obese or pregnant. People with liver disease such as cirrhosis may also develop swollen hemorrhoids due to increased pressure in the veins of the intestine.

Many people believe that swollen hemorrhoids can be caused by sedentary occupations, sitting on hard, cold surfaces, prolonged standing, or diarrhea. These conditions are not responsible for inflamed or aggravated hemorrhoids, but can be causes of a condition called thrombosed external hemorrhoid. This is actually a hematoma or blood-filled swelling due to the rupture of an external hemorrhoidal vein. It follows a sudden increase in pressure within the vein and usually occurs after heavy lifting, coughing, sneezing, exercise, straining at stools, or giving birth and can cause extreme pain and discomfort.

Diagnosing swollen or thrombosed hemorrhoids involves a physical examination, and a procedure called anuscopy is also needed to detect the presence of internal swollen or bleeding hemorrhoids. A small instrument is inserted into the rectum to allow the doctor to check for hemorrhoids and associated inflammation. Proctosigmoidoscopy, which also involves inserting an instrument higher up into the rectum, may be done to rule out other diseases.

The anus, the opening at the lower part of the rectum through which bowel movement pass from the body, is warm, moist and richly endowed with sensory nerve receptors. These nerve endings register feelings of itchiness when they are mildly stimulated, and feelings of pain when the irritation is more intense. Thus, anal itching is often interspersed with deeply aggravating pain.

Frequently, the itching is due to temporary, often trivial events, such as eating foods that cause irritation. Common offenders include red pepper and other warm spices. Atopic dermatitis which may be caused by an allergic reaction to perfumes and other chemicals in soaps, bubble baths, spays and even toilet paper, can cause intense anal itching. Infectious organisms such as the candidas fungus, or various bacteria also cause anal itching. Diabetes and psoriasis also can cause itching.

Contrary to popular belief, hemorrhoids do not in themselves cause itching. The itching that many individuals having swollen hemorrhoids experience is often due to hygienic practices, such as inadequate wiping, or to the medications used to relieve discomfort from the swollen hemorrhoids themselves. In most instances anal itching is not dangerous. But it can be distracting and debilitating and needs to be relieved as soon as possible.

A wide variety of over-the-counter drugs are sold to relieve anal itching and pain. Few have been shown to be safe and effective according to Food and Drug Administration criteria. Hydrocortisone creams and ointments (0.5%) are effective for itching outside the rectum, but should not be used inside. Anesthetics such as benzocaine ointment or parmoxine hydrochloride, in cream or jelly form, also can be used in this way.

Commercial suppositories and ointments have no overall effect on swollen hemorrhoids and itching because the swollen hemorrhoids and the itching points are located under the skin or under, the membrane, and whatever is put on top of the skin or membrane can have little effect on what is under it.

Additional conditions that also cause pelvic floor pain and can benefit from the novelty of this configuration may include Pudendal Neuralgia, bicycle seat neuropathy, prostatitis, testicular pain, irritable bowel syndrome, anal abscesses, anal fissures, anal fistulas, interstitial cystitis, animus, dyssynergia, pelvic muscle spasms, pelvic congestion, vulvar atrophy, vulvodynia, post-partum pain, endometriosis, groin injuries, dysmenorrhea and vaginal atrophy.

Further conditions that may occur in the feet and/or hands or other distal portions of the body as a result of diseases such as diabetes or burns—generally areas of low blood supply. Treatments for swelling and diabetic foot ulcers and/or neuropathy, gout, and toe fungus may include medications and bathing in various medications, but may be difficult to manage or maintain.

Treatments are generally applied to a patient that is in a still or seated position. For persons with an active lifestyle, or a job that requires much movement, these therapies can be problematic and may cause the patient to defer or refuse treatment in favor of livelihood or lifestyle considerations.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
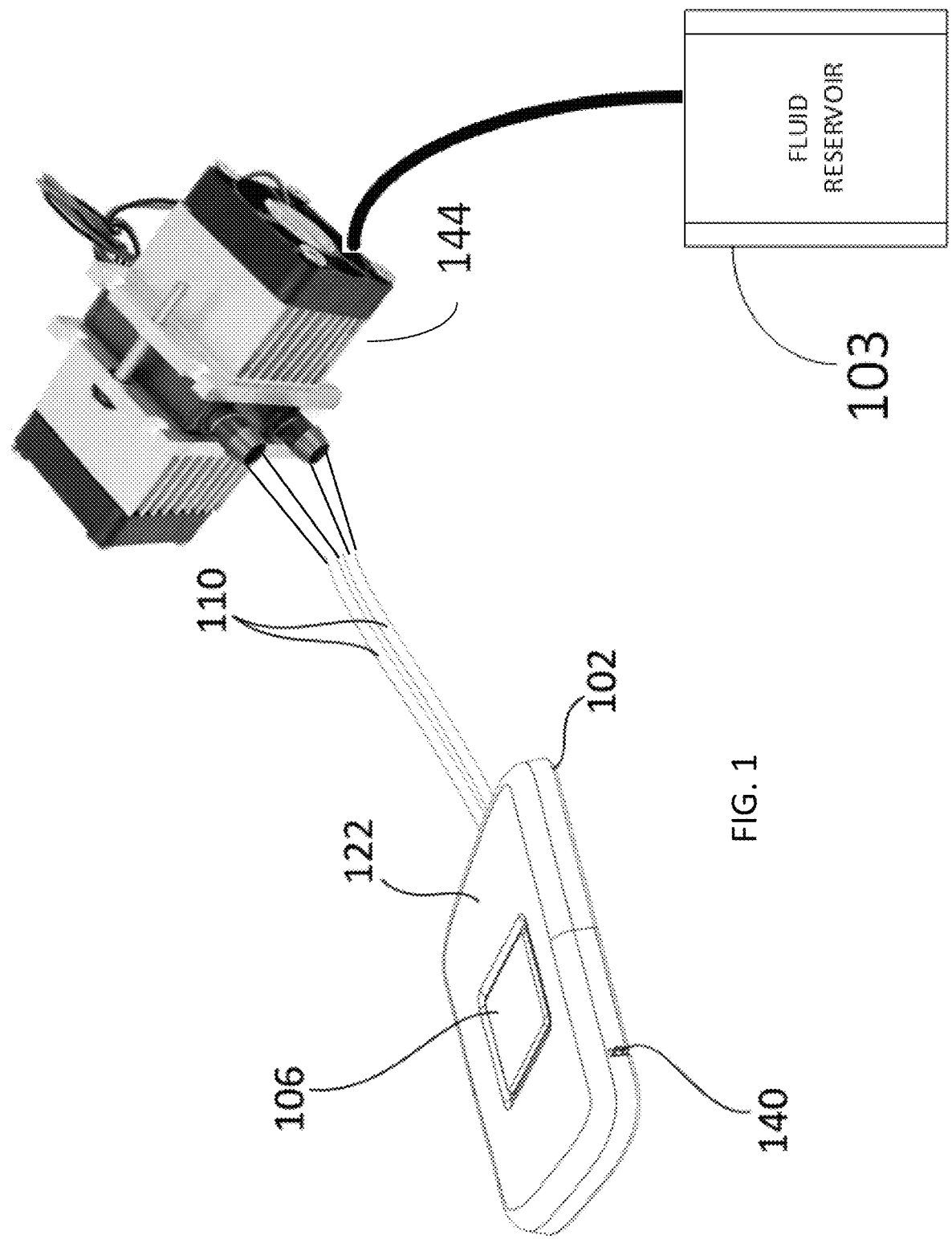
FIG. 1 is an isometric view of an embodiment of the Thermal contrast therapy system utilizing an active heating and cooling support system

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" refers to top and "lower" refers to the bottom. As a non-limiting example, the upper end of a vertical shaft is the top end of the vertical shaft.

As used herein, "ambient environment" refers to the natural environment surrounding the invention.

As used in this disclosure, an "aperture" is an opening in a surface. Aperture may be synonymous with hole, slit, crack, gap, slot, or opening.

As used herein, "approximate" and "approximately" indicate that information that is being presented is not critical for proper functioning of the invention and that the information is being provided only to assist in a better understanding of some physical characteristic of an embodiment of the invention. As a non-limiting example, a device that is described as "cubical and approximately 1 inch long on each side" is not required to be precisely 1 inch long on each side and the reader may understand that the device will likely fit in their pocket.

Throughout this document the terms "battery", "battery pack", and "batteries" may be used interchangeably to refer to one or more wet or dry cells or batteries of cells in which chemical energy is converted into electricity and used as a source of DC power. References to recharging or replacing batteries may refer to recharging or replacing individual cells, individual batteries of cells, or a package of multiple battery cells as is appropriate for any given battery technology that may be used. The battery may require electrical contacts which may not be illustrated in the figures.

As used in this disclosure, a "cavity" is an empty space or negative space that is formed within an object.

In this disclosure, "compress" refers to forcing into a smaller space or to apply pressure.

As used herein, the words "control" or "controls" are intended to include any device which can cause the completion or interruption of an electrical circuit; non-limiting examples of controls include toggle switches, rocker switches, push button switches, rotary switches, electromechanical relays, solid state relays, touch sensitive interfaces and combinations thereof whether they are normally open, normally closed, momentary contact, latching contact, single pole, multi-pole, single throw, or multi-throw.

As used in this disclosure, a "control system" is a first device or system that manages and regulates the behavior or operation of a second device or system.

As used in this disclosure, the word "correspond" indicates that a first object is in some manner linked to a second object in a one-to-one relationship or that one or more properties shared by two or more objects match, agree, or align within acceptable manufacturing tolerances.

As used herein, the words "couple", "couples", "coupled" or "coupling", refer to connecting, either directly or indirectly, and does not necessarily imply a mechanical connection.

As used herein, the word "desired" refers to a specific value or action within a range of supported values or action. A "desired" value or action indicates that a range of values or actions is enabled by the invention and that a user of the invention may select a specific value or action within the supported range of values or action based upon their own personal preference. As a non-limiting example, for a fan that supports operational speed settings of low, medium, or high, a user may select a desired fan speed, meaning that the user may select low, medium, or high speed based upon their needs and preferences at the time of the selection.

As used in this disclosure, "elastic" refers to a material or object that deforms when a force is applied to stretch or compress the material and that returns to its relaxed shape after the force is removed. A material that exhibits these qualities is also referred to as an elastomeric material.

As used herein, "elastomeric polyurethane" refers to a class of polyurethane material that has the characteristics of rubber. Being a polyurethane, it is a polymer derived from the reaction between a molecule with an isocyanate (R—N=C=O) functional group and a molecule with multiple alcohol groups (R—OH), called a polyol. The choice of isocyanate and polyol are what makes one polyurethane elastomeric rather than another type of polyurethane.

As used herein, "energize" and/or "energization" refer to the application of an electrical potential to a system or subsystem.

As used herein, "filling", or "refilling", refers to the act of placing a first item into a second item whether the quantity of the first item fills the second item or not. As non-limiting examples, the first item may be a liquid, such as water or gasoline, or a granulated solid, such as sand or coffee beans. As non-limiting examples, the second item may be a bin, a bottle, a tank, or another type of container.

As used in this disclosure, "flexible" refers to an object or material which will deform when a force is applied to it, which will not return to its original shape when the deforming force is removed, and which may not retain the deformed shape caused by the deforming force.

As used herein, "front" indicates the side of an object that is closest to a forward direction of travel under normal use of the object or the side or part of an object that normally presents itself to view or that is normally used first. "Rear" or "back" refers to the side that is opposite the front.

As used herein, the words "invert", "inverted", or "inversion" refer to an object that has been turned inside out or upside down or to the act of turning an object inside out or upside down.

As used herein, "lattice structure" refers to a structure having a supporting lattice form with openings in the lattice that enable gaseous medium movement through the lattice structure.

As used herein, "mate" refers to a retaining, coupling, connecting, interlocking, or interfacing at a predefined interface.

As used herein, "neoangiogenesis" refers to the process of making new vascular structures through microfissures in the venous structures.

As used herein, "pair", "paired", and "pairing" refer to a connection established between two wireless devices or to the process of establishing such a connection.

As used in this disclosure, a "pump" is a mechanical or electromechanical device that uses suction or pressure to raise or move fluids, compress fluids, or force a fluid into an inflatable object. As non-limiting examples, fluids may include both liquids, such as water, and gases, such as air.

As used in this disclosure, "remote control" refers to the establishment of control of a device from a distance or to the controlling device itself. Remote-control is generally accomplished through the use of an electrical device that generates electrically based control signals that are transmitted via radio frequencies to the device. Some remote controls may use infrared light to communicate with a device.

As used in this disclosure, a "reservoir" refers to a container or containment system that is configured to store a liquid, gas, or gel.

As used herein, "smart device" refers to a portable electrical device comprising at least a processor, display, input device, and network connection. The input device is generally a touch screen, keyboard, or voice recognition. The network connection is generally wireless. Non-limiting examples of smart devices may include smartphones, tablets, personal digital assistants, laptop computers, and smartwatches.

As used herein, a "tablet computer" or "tablet" refers to a mobile computing device packaged as a single, monolithic unit—similar in appearance to a paper tablet. Typically, tablet computers have a touch sensitive, flat video display covering most of the front surface and do not have a keyboard; although many tablet computers may be mated with a separate keyboard accessory. Tablet computers generally comprise one or more microprocessors, memory, and a rechargeable battery internal to the tablet. Most tablet computers comprise a wireless network connection, typically via a WiFi interface. Many tablet computers comprise an internal camera, microphone, and one or more audio speakers. Interaction between the user and a tablet computer is generally via the touch screen using a stylus or fingers and may involve the use of 'gestures' which are specific motions on the touch screen which are interpreted by the tablet computer to magnify or shrink the display, open, close, or switch between applications, scroll, or perform other tablet computer functions.

As used in this disclosure, "therapeutic" is an adjective that refers to a medical, ameliorative, or hygienic substance, process, or procedure.

As used in this disclosure, a "tube" or "tubing" refers to a hollow cylindrical device that is used for transporting liquids and/or gases. In this disclosure, the terms inner diameter and outer diameter are used as they would be used by those skilled in the plumbing arts. The line that connects the center of the first base of the cylinder to the center of the second base of the cylinder and is equidistant from the outer surface of the tube for its entire length is referred to as the centerline of the tube. When two tubes share the same centerline, they are said to be aligned. When the centerlines of two tubes are perpendicular to each other, the tubes are said to be perpendicular to each other. As used here, "tubing" refers to a tube that is flexible or resilient.

As used in this disclosure, a "valve" is a device that is used to control the flow of a fluid, either gas or liquid, through a pipe or to control the flow of a fluid into and out of a container. Some valves may have multiple ports and may allow the diverting or mixing of fluids.

The present invention relates to physical therapy thermal contrasting systems. In particular, the invention relates to thermal contrast therapy systems which may be applied to stationary perineal/pelvic applications, ambulatory perineal/pelvic applications, as well as podological and/or distal hand applications for treatment of extremities. The thermal contrasting thermal system herein described utilizes a twin thermal tank to deliver both heating and cooling therapies to affected areas. Additionally, the twin thermal tank may be utilized to support opposing thermal treatment modes simultaneously.

The prostate gland is located below a man's urinary expandable membrane. The prostate gland is connected by the urethra, which is a tube that starts at the urinary expandable membrane and goes through the middle of the prostate gland and carries urine out through the penis. As some men grow older, the prostate tissue surrounding the urethra grows in size and constricts the flow of urine from the urinary expandable membrane to the penis. This can cause a man extreme pain and discomfort.

In addition to providing therapeutic relief for hemorrhoid sufferers, the system and method herein presented may also present treatment options for those suffering from Nerve conditions, such as pudendal neuralgia, Dyssenergia, Bicycle Seat neuropathy and prostatitis, Pelvic Floor Hypertensiveness such as Anismus, Chronic Pelvic Pain syndrome, and Spastic Pelvic Floor syndrome, Raw Nerve conditions such as IBS and Anal Abcesses, Female Specific conditions such as Vulvar Atrophy, Vulvadynia, and personal pamper, Post-Surgical Relief, such as Ano-Rectal Surgery, External Hemorrhiod Surgery, Post-Partum Repair, Groin Surgery, and Post Prostate Surgery, and Sports Injuries incurred when engaging in Ice Hockey, Soccer, Football, Tennis, Wrestling, Gymnastics, and other strain induced groin injuries.

The thermal contrast therapy system may provide treatment options for ambulatory treatments, where the thermal contrast therapy system may be worn by a user during the user's everyday activities while still providing heating or cooling therapies to an affected area of the user's body. Additionally, the thermal contrast therapy system may provide therapeutic action for sufferers of diabetic neuropathy, gout, toe fungus—Onychomycosis.

The system and method for providing therapy herein presented may comprise a thermal contrast therapy system. The invention may further comprise a method of providing thermal contrast therapy. The Thermal contrast therapy system may comprise a human interface device, an expandable thermal transfer membrane, a fluid tubing, a pump, and a reservoir. Although useful for applying any combination of heat, cold, and pressurized compression, to a therapy recipient, the Thermal contrast therapy system described below demonstrates particular utility for treating anal-prostate-perineal and vaginal areas that are sore, strained, irritated, thrombosed, injured or otherwise overly sensitized, whether in a stationary, seated position or in an ambulatory manner when worn by a user, and may be used to treat conditions of the extremities that may respond to heat or cold treatments. Such areas are hereafter referred to as a therapy site. The Thermal contrast therapy system is described below in the context of providing "therapy" to the therapy recipient, however, it should be understood that the Thermal contrast therapy system may be equally well suited for providing any combination of heat and cooling contact therapy for what may be considered non-therapeutic purposes.

This invention relates to an improved device where the unique configuration of expanding fluidic membrane provides the means of temporary relief. The device is also capable of being reused.

Applying warm and/or cold (contrast therapy) to inflamed or irritated areas of the human body as a therapeutic treatment is well known. For example, ice packs may be applied to a sprained ankle to reduce swelling, or a container filled with warm water may be applied to a sore back to help loosen and relieve the back muscles. The potential effectiveness of a warm or cold treatment increases as the level of control for the treatment increases. In particular, for injuries to the regions of swollen hemorrhoidal, perineal, vaginal and prostate, the effectiveness depends on the ability to control the temperature, pressure, and gentleness of local application and duration of therapy applied to the injured surface area in direct contact. Due to the extreme nerve sensitivities brought about by, for example, a swollen hemorrhoidal flare up condition, if the density, hardness or durometer and/or other features of currently used methods are too great when applied to the areas of focus, the level of discomfort can be so high as to render the effective utilization of current methods unacceptable. Therefore, a method for more precisely controlling the temperatures and pressures over a longer period of time than all previous efforts of prior art, while maximizing the area of contact are applied to said region of interest with least amount of pain and discomfort are highly desirable.

The Thermal contrast therapy system may also be expanded to provide additional therapeutic actions through a combination of light, acoustic or sonic energy, medicament coatings, and/or on body Gel flow thermal delivery. The Thermal contrast therapy system may also provide a seat, foot covering, hand covering or other device that will be in contact with a portion of the human body—with an active fluid delivery system that delivers the fluid into a membrane that comprises the exterior surface of the Thermal contrast therapy attachment portion. There is in the currently filed application a reference to a diverter in the seat that could be used to send the fluid into the membrane.

To accomplish the various treatment therapy modes, the system may have lattice elements placed within the membrane that is in contact with the treatment area. The lattice elements, which may have the form of replaceable pods, may be constructed with fluid channels where the lattice supports the infusion of therapeutic fluids by perfusion through the structure of the lattice. The lattice pods, again, may be encased within a lattice covering that is impermeable to the fluid being perfused.

To support the fluid delivery, a twin cavity separable reservoir with a thermal tank having two temperature-controlled fluid cavities, a hot side and a cold side, may be connected to the lattice pods. In an embodiment, the lattice may be a very spongy, durable shape and may pump air or fluid through the lattice through the use of pups or fans. The fans may allow air flow using tube axial fans with the cavity resting inside the Thermal contrast therapy containment tank.

In an embodiment, the Thermal contrast therapy system may also be able to support an ambulatory pelvic floor device, additionally a foot boot, hand wrap, or other extremity covering device.

In an embodiment, the system may include thermal transfer devices, a pipe system ergonomically designed to transfer heated or cooled fluid from the dual temperature tank to the heat transfer membrane to transfer the heat or cooling from the temperature transfer fluid for delivery to the treatment area. Transferring heat or cooling in this manner reduces necrosis or injury. In an embodiment, the thermal transfer device may be adapted to contain a gel where the gel is encased in a thicker heat permeable membrane. The gel may be adapted to flow through the thick heat permeable membrane to provide for longer heat or cooling transfer times.

In an embodiment, additional therapeutic modes may include an acoustic therapy capability. This therapeutic mode may utilize an acoustic generation device to drive acoustical energy into the Thermal contrast therapy attachment, where the attachment may be a seat coming into contact with the pelvic floor, through the fluid membrane to the human anatomy, or through the boot or other extremity covering device. This treatment method has been shown to be effective to treat erectile disfunction.

In an embodiment, the Thermal contrast therapy system may also contain SpO2, Oxygen Saturation, sensors to give feedback to the application to monitor usage remotely. This application may be used to monitor progress in treatment effects when the Thermal contrast therapy system is in active use. The SpO2 sensors may be integrated to provide feedback and to control logic to display real-time data related to patient usage patterns for performance and tracking of in-home use of the system.

In an embodiment, membranes are replaceable—the membranes may be created as medicament coated fluid membranes. The temperature of the reservoir may be controlled by various mechanisms. In some embodiments, the cold reservoir may be adapted to receive ice that may melt in the cold reservoir, thus decreasing the temperature of the fluid in the cold reservoir. A receptacle has a reservoir aperture that may be suitable for easily receiving ice. In some embodiments, the cold reservoir may include a cooler for cooling the fluid held in the cold reservoir. It is within the scope of the invention to use virtually any other suitable method for cooling the fluid held in the reservoir. The cold reservoir may include insulation to limit heat transfer between the fluid held by the cold reservoir and the external environment.

In a non-limiting example, the minimum temperature of the fluid in the reservoir may usually be limited to approximately 32.5 to 45 degrees Fahrenheit, although such a limitation is not necessary. In particular, it has been found that a temperature of about 35 to 42 degrees Fahrenheit is an appropriate minimum temperature. In a non-limiting example, the Thermal contrast therapy system twin mode tank may perfuse liquids that have been heated to temperatures as high as 11 degrees F. and as low as 33 degrees F., and may provide both heated and cooled fluids simultaneously. Although water is usually used as the fluid, it is within the scope of the invention to use other suitable fluids. Such fluids may be selected for particular applications based on their specific heat, viscosity, freezing point, or combinations thereof.

The human interface device may be an enclosure for the membrane, a transfer port, and other components of the Thermal contrast therapy system. The human interface device may comprise the membrane, a sit surface, a foot HID, a hand HID the transfer port, and a plurality of voids. The human interface device may be adapted for the therapy recipient to place the therapy site adjacent to the membrane. As a non-limiting example, the human interface device may be adapted for the therapy recipient to sit upon the sit surface such that the membrane is directly below the therapy site. As a non-limiting example, the sit surface may be a top surface of the human interface device. The sit surface may be contoured to complement the therapy site. In some embodiments, the sit surface may be heated and/or cooled.

In some embodiments, portions of the human interface device may be fabricated from a lattice of elastomeric polyurethane such that the human interface device provides intrinsic airflow at the dermal surfaces, cushioning and suspension. As a non-limiting example, the sit surface may be fabricated from a lattice of elastomeric polyurethane. This lattice structure may be fabricated of various different materials or methods of manufacture to allow for a composition of lattice structures that would enable gaseous medium movement, or airflow. The lattice structure of the human interface portion may have regions that are smooth and not lattice to support thermal membrane and the need to protect and insulate specific areas of the human interface portion from direct contact with the human anatomy to protect against high thermal externally radiating losses. The lattice structure may also incorporate pockets or voids to accommodate various types and sizes and available flow rates of tube-axial type positive airflow devices to provide therapy for various conditions. In a non-limiting example, the lattice structure may also incorporate channel structures that permit fluid delivery to the portion of the human anatomy in contact with the lattice structure. This fluid delivery provides for delivery of thermal therapy from the fluid reservoir of the Thermal contrast therapy system.

The membrane may be an expandable interface between the human interface device and the therapy site. The therapy fluid may flow into and out of the membrane via fluid transfer openings. The membrane may expand due to pressure from the therapy fluid and may conform to contours of the therapy site. Heat may transfer through the membrane, either from the therapy fluid to the therapy site or from the therapy site to the therapy fluid, such that the therapy site may be warmed or cooled.

A membrane void in the human interface device may be dimensioned to retain a space for the membrane. However, the volume of the membrane may be controlled by changing a power level, and thus the pumping pressure, from 10% to 100% via the remote-control device. Furthermore, the membrane may be constructed from various appropriate, sanitary flexible materials, such as polyisoprene, urethane, silicone or latex rubber, which may permit a membrane expansion in response to the pressure of fluid within the membrane. The membrane may stretch and naturally return to an unstretched disposition. When stretched, the membrane is at an increased tension, which may be used to contact directly under pressure around the therapy site.

In an embodiment, a lattice attachment pad may allow for similar features as previously expressed at lower cost and in a more efficient manner. The lattice attachment pad may allow for an add-on module to a standard molded Thermal contrast therapy device human interface.

The transfer port may be an interface between the membrane and the fluid tubing. The transfer port may simplify the interconnection of the fluid tubing to the membrane. In some embodiments, the transfer port may comprise one or more transfer port to hid interfaces for coupling the transfer port to the membrane.

In some embodiments, the transfer port may comprise a thermostat for sensing the temperature of the therapy fluid as part of the control system. The thermostat may communicate the temperature of the therapy fluid to software, a microcontroller, a power supply, to the pump, to mixing valves, or combinations thereof such that an adjustment to the temperature and/or the power level may be made in order to keep the therapy fluid at a pre-set temperature. As a non-limiting example, the thermostat may be designed to receive manual input of a desired therapy temperature and adjust the mixing valve to yield the therapy fluid with that temperature. Accordingly, the thermostat may include a temperature measuring device such as a thermistor, thermometer, or thermocouple. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of warm and cold fluids delivered from the mixing valve. As a non-limiting example, the thermostat may be programmed to provide alternating warm therapies that last for five minutes at 105 degrees Fahrenheit and cold therapies that last for 5 minutes at 40 degrees Fahrenheit. It should be understood that the thermostat may be programmed for therapies of different durations and/or temperatures.

The plurality of voids may be cavities within the human interface device where components of the Thermal contrast therapy system may be placed for protection and for concealment. The plurality of voids may comprise the membrane void, a power cable void, a pump containing void, a power supply containing void, a fluid tubing containing void, and a transfer port containing void. The membrane void may be a cavity on the top of the human interface device intended for placement of the membrane. The power cable void may be a cavity on the bottom of the human interface device intended for placement of a power cable. In some embodiments, the power cable void may provide a path for the power cable to run between the power supply containing void and the pump containing void. The pump containing void may be a cavity on the bottom of the human interface device intended for placement of the pump. The power supply containing void may be a cavity on the bottom of the human interface device intended for placement of the power supply. The fluid tubing containing void may be a cavity on the bottom of the human interface device intended for placement of the fluid tubing. The transfer port containing void may be a cavity on the bottom of the human interface device intended for placement of the transfer port. The plurality of voids may extend to a side of the human interface device and/or may extend through the human interface device. As non-limiting examples, the fluid tubing containing void may extend to a side of the human interface device such that the fluid tubing may exit the human interface device and the transfer port containing void may extend to the membrane void via the one or more transfer port to hid interfaces.

The fluid tubing may comprise a fluid delivery tube, a fluid return tube, and a pair of couplers/or straight pass-thru to the fluid reservoir pick up and return. The fluid tubing may transport the therapy fluid between the reservoir and the transfer port. The pair of couplers may detachably couple the fluid tubing to the reservoir. Specifically, the fluid delivery tube may transport the therapy fluid from the reservoir to the transfer port. After the therapy fluid passes through the membrane via the transfer port, the fluid return tube may transport the therapy fluid back to the reservoir. The human interface device may be easily coupled and decoupled from the fluid tubing via the pair of couplers/or straight pass-thru to the fluid reservoir pick up and return. The pair of couplers may comprise an intake port and an outflow port. The intake port and the outflow port may detachably couple the fluid tubing to bulkhead ports located on a coupling assembly. The intake port may terminate the fluid delivery tube and may detachably couple the fluid delivery tube to the coupling assembly. The outflow port may terminate the fluid return tube and may detachably couple the fluid return tube to the coupling assembly.

Expansion of the membrane may facilitate thermal exchange between the therapy site and the therapy fluid. As a non-limiting example, when a cold therapy is administered, heat from the body of the therapy recipient may heat the therapy fluid, which in turn cools the therapy site. Similarly, when a warm therapy is administered, the therapy fluid may transfer heat to the therapy site. The therapy may be enhanced by moistening the membrane to provide a moist therapy. Furthermore, the fluid may also be pulsed through the membrane, adding a therapeutic massage aspect to the therapy site. In this therapeutic example, acoustical energy may also be focused into the membrane via the delivery fluid contained within the human interface device in order to improve erectile venous blood flow. Furthermore, usage of ergonomically humancentric anal and vaginal cavity devices, utilizing over molded/integrated thermally transmissive devices known commonly as heat pipes, may deliver available thermal energy to internally located devices via the membrane supported by the Human Interface Device (HID).

In an embodiment, treatments may include the delivery of light energy to an affected area. Light from the infrared, through visible light, and into ultraviolet light may be provided as treatment to affected areas dependent upon they type of damage to be treated and the light energy that will deliver the most efficacious treatment for the condition.

Fluid paths described herein may utilize flexible tubing or may alternatively implement another suitable fluid transport mechanism. As a non-limiting example, some or all of the fluid paths may alternatively be defined by inflexible fluid conduits. The fluid paths may include filters, flow restrictors, and/or check valves. Filters may help prevent flow blockages resulting from jammed ice or other substances, and check valves may be used to prevent backflow in the system. The rate of fluid flow may be at least partially controlled by flow restrictors or the power level setting of the pump.

The intake port and the outflow port may each include one male valve and/or one female valve, which are configured to mate with a corresponding female and/or male valve. The human interface device may be easily coupled and decoupled from the fluid tubing.

The pump may circulate the therapy fluid through the Thermal contrast therapy system. The pump may be positioned in several locations along the fluid tubing. As a non-limiting example, the pump may be positioned within the pump containing void. Alternatively, the pump may interpose the mixing valve and the bulkhead output. In some embodiments, more than one pump may be utilized. The pump may be integrated into a reservoir lid of the reservoir. The pump may be powered according to the desired application. In a preferred embodiment, a pump therapy fluid capacity may be sized to be most effective for the condition to be treated. The pump may be a reciprocating pump, a rotary pump, or virtually any other suitable pump.

In some embodiments, the pump may be configured to pulse the therapy fluid through the therapy human interface device. Such a pulsing action may be translated into a therapeutic massage at the therapy site via the human interface device. As the pulsing fluid circulates through the human interface device, the membrane may pulsate due to varying pressure. Pumps designed to pulse fluid may be further enabled to adjust the relative magnitude of the pulsing to correspond to different intensities of therapeutic massages. The relative intensity of the pulsations may be automatically or manually coordinated to correspond to a particular temperature of treatment. As a non-limiting example, a vigorous massage may be applied during a warm treatment while a milder massage is applied during a subsequent cold treatment.

Use of the Thermal contrast therapy system may include circulating the therapy fluid with the initial therapy temperature through the human interface device. The therapy fluid may be circulated in a pulsing stream, so as to impart a vibration that is useful in providing a therapeutic massage. Of course, the flow may instead be smooth. Use of the Thermal contrast therapy system may include applying the human interface device to the therapy site on the therapy recipient. The temperature of the therapy fluid may be translated through the fluid tubing to the membrane. As a non-limiting example, if the initial temperature of the therapy fluid is relatively warm, for instance 110 degrees Fahrenheit, the human interface device may be used to heat the therapy site on the therapy recipient. Similarly, the therapy fluid with a relatively cold therapy temperature, such as 40 degrees Fahrenheit, may be used to cool the therapy site. The human interface device may be applied to the therapy recipient by using the membrane to compress the human interface device against an injured therapy site.

Use of the Thermal contrast therapy system may further include returning the therapy fluid to at least one of the volumes of warm fluid and the volume of cold fluid. Returning the therapy fluid to either or both of the volumes of warm and cold fluids allows the therapy fluid to be recycled. A returned fluid may then be heated and/or cooled, and eventually may be recirculated to the human interface device. In this manner, a limited volume of fluid in a system may be used to provide an ongoing therapy. The fluid may be repeatedly heated and/or cooled, and thus the character of the treatment may be continually changed.

Use of the Thermal contrast therapy system may also include selecting relative amounts of the warm and cold fluids to mix as the therapy fluid with a desired Anal-Perineal-Prostate-Vaginal-Pelvic Floor contrast therapy temperature different than the initial therapy temperature. By changing the relative amounts of warm and cold fluids, the resulting temperature of the therapy fluid may be changed, which changes the therapy received by the therapy recipient. It is within the scope of the invention to make such temperature changes quickly through the use of quick release fluid couplings or with automatic electrically operated valves. Circulating a thermally contrasting fluid with the Thermal contrast therapy system allows the therapy recipient to experience a cold treatment immediately after a warm treatment or a warm treatment immediately after a cold treatment. It should be understood that the period of change between respective treatments is ideally very small, such as under two minutes. This process may be repeated one or more times, and each time the relative amounts of the power level delivering greater or lesser volumes and resultant pressures to injured tissues/muscles of warm and cold fluids may be selected to result in a desired therapy temperature.

The reservoir may hold the therapy fluid. The reservoir may comprise the receptacle and the coupling assembly. The receptacle may be a cylindrical container with the reservoir aperture at the top. The coupling assembly may comprise the reservoir lid and the bulkhead ports. The coupling assembly may selectively couple and decouple the fluid delivery tube and the fluid return tube. The reservoir lid may cover the receptacle and may seal the receptacle to prevent leakage of the therapy fluid. The bulkhead ports may couple to the intake port and the outflow port such that the therapy fluid may be drawn from and returned to the reservoir.

The reservoir may be dimensioned to hold virtually any volume of the therapy fluid. As a non-limiting example, the receptacle may hold one liter of the therapy fluid. When increased thermal stability is desired, the reservoir may be larger than one liter to provide an increased capacity for the therapy fluid.

The reservoir may be designed to hold a warmed thermal fluid of approximately 100 to 118 degrees Fahrenheit. Pressure from the therapy fluid flowing through the membrane may stretch the membrane such that the membrane conforms to the contours of the therapy site. The therapy fluid in the reservoir may be heated by a heater that is incorporated into the reservoir or the therapy fluid may be brought to temp elsewhere using an external heat source and then placed into the reservoir. The reservoir may be thermally insulated to retain the temperature of the therapy fluid as long as possible.

In some embodiments, the reservoir may be a single component used for both cold fluid therapy and warm fluid therapy. In some embodiments, a cold fluid reservoir and a warm fluid reservoir may be provided and may have differentiated features and sizes. As a non-limiting example, the warm fluid reservoir may comprise the heater which the cold fluid reservoir does not provide.

The flow rate of fluid through the warm reservoir may correspond to the temperature of treatment being applied, with greater flow rates occurring during desired warmer treatments due to some thermal losses of exposed tubing to the ambient environment. During some warm treatments, the heater may have limited time to increase the temperature of the fluid because the fluid quickly passes through the warm reservoir. For this reason, the heater may be powered so as to increase the temperature a desired amount within that constrained timeframe. However, the heater does not need to completely heat the fluid from a minimum temperature to a maximum temperature in such a timeframe, although it is within the scope of the invention to do so. The therapy fluid may cool in the process of being pumped from the reservoir to the membrane and through the therapy site but may return to the reservoir while still at a temperature that is above the starting temperature of the therapy fluid. The starting temperature of the therapy fluid is defined to be the temperature of the therapy fluid that was placed into the reservoir. Thus, the net temperature of the fluid may incrementally increase as it repeatedly circulates through the reservoir. The maximum temperature of the fluid in the reservoir may be limited to approximately 100 to 118 degrees Fahrenheit, although such a limitation is not required. In particular, it has been found that a warming temperature of about 105 degrees Fahrenheit may be optimal for warm fluid therapy.

The power supply may provide power to operate the Thermal contrast therapy system. As non-limiting examples, the power supply may provide power for the heater, the cooler, the pump, the thermostat, and a display. In some embodiments, the power supply may utilize alternating current, while in other embodiments, the power supply may utilize direct current. Some embodiments may be configured to operate with either AC or DC power. As a non-limiting example, the Thermal contrast therapy system may include a DC heater and pump designed to draw power from either a battery or an electrical outlet via an AC/DC converter. Batteries used to power the Thermal contrast therapy system may be externally connected to the system, and/or housed within the system. The Thermal contrast therapy system may be powered from alternative power sources as well. As non-limiting examples, the Thermal contrast therapy system may be powered by a rechargeable battery pack, an automobile battery via an automotive cigarette lighter jack, a USB Port, solar panels, or from a generator.

The power supply may comprise a signal receiver. The signal receiver may receive a signal that is transmitted by the remote-control device. The signal receiver may be operable to turn power to the human interface device on and off. The signal receiver may be operable to change the power level of the power supply.

The remote-control device may provide a power level interface and may remotely adjust the fluid speed and pressure delivered by the pump. The remote-control device may be adapted to be used by an operator. As non-limiting example, the operator may be the therapy recipient or a therapist. The power supply, the remote-control device, and the pump may comprise a control system that regulates the maximum flow rate and/or temperature of the therapy fluid in the reservoir. The control system may also be designed to maximize thermal efficiency to limit energy requirements.

The operator may interact with the power level interface of the remote-control device and command the remote-control device to send a wireless message to the Thermal contrast therapy system that establishes the power level for the pump. The power level may indicate a relative magnitude of a desired therapy pumping pressure. As a non-limiting example, the power level interface may include a series of icons representing relative percentages of pressure from 10% to 90%. As non-limiting examples, the signal communicated between the remote-control device and the signal receiver may be based upon an RF or IR carrier and may be modulated to convey a specific command.

In an embodiment, additional therapeutic results may be obtained through a combination of therapies delivered in connection with the thermal fluid therapy. Additional therapies may include the delivery of sonic energy through acoustic devices, light energy delivered through one or more light sources, and medicament delivery through medicament coatings on the membrane in contact with the human user.

In an embodiment, acoustic energy may be delivered through the fluid medium to a fluid membrane transfer element. A sonic emitter provides the sonic energy through one or more active sound emitters embedded within the structure of the Thermal contrast therapy system. In a non-limiting example, acoustical or sound energy transmissions may be used to affect arterial plaque reductions using vibration, as well as to introduce new smaller micro fissures in the venous structures through neoangiogenesis that may assist in inducing deeper and more lasting therapeutic effects.

In an embodiment, various compact lumen and/or visual radiant emissive technologies may be used to deliver light energy through the fluid barrier as previously indicated.

In an embodiment, the membrane in contact with the human user may be further enhanced through the addition of a coating or a carrier medium of medicament to the membrane. The addition of a medicament leverages and further supports improved applications of therapy that can benefit from the thermal ranges of application to induce human dermal uptake. Additionally, the Thermal contrast therapy system may be configured to be worn by a user during therapy sessions, permitting the user to be ambulatory during such use.

In an embodiment, the Thermal contrast therapy system provides an electronically controlled pulsing action of the membrane via motor pumping action to induce massaging effects to region of therapy application. This action is also provided to a Foot Bed therapy delivery device that is supportive of foot maladies such as diabetes and gout, whereas increasing vasoconstriction/vasodilation would improve/assist the body's ability to heal. In this embodiment, a foot bed interface device may support "wet free" softening of the toenail bed to induce medicament penetration of the toe nail without having to remove the toenail. The Thermal contrast therapy system also provides heat and cooling to affected areas of a hand or wrist to assist with healing sprains, treating arthritis, and treating other conditions of the hands and wrists.

In an embodiment, the Thermal contrast therapy system may establish a data communication with a server, smart device, laptop, or other computer system to transmit sensor, time and device specific data (Internet protocol IPv4/IPv6) via IoT Connected element directly to physician monitoring networks. Software to include controls that are patient controlled via UI/UX interface on smartphone type systems and may be remotely controllable by physician of record.

In some embodiments, the remote-control device may be a smart device. As non-limiting examples, the smart device may be a smartphone or tablet computer.

In some embodiments, the human interface device may comprise a diverter. The diverter may direct the therapy fluid to the sit surface such that the sit surface may be heated and/or cooled.

The method of using the Thermal contrast therapy system may comprise placing the therapy site against the human interface device, pumping the therapy fluid from the reservoir, through a membrane of the human interface device, and back into the reservoir, expanding the membrane against the therapy site, and exchanging heat between the therapy fluid and the therapy site via the membrane.

The method of using the Thermal contrast therapy system may further comprise monitoring the temperature of the therapy fluid and controlling the temperature of the therapy fluid to attain a targeted temperature range. As a non-limiting example, monitoring the temperature of the therapy fluid may be performed by the thermostat. Controlling the temperature of the therapy fluid to attain a targeted temperature range may be performed using the heater, the cooler, by modulating the flow rate using the power level, or combinations thereof. As a non-limiting example, a desired temperature range for the therapy fluid may be established using the remote-control device and the temperature of the therapy fluid may be monitored as the therapy fluid circulates within the Thermal contrast therapy system. If the temperature of the therapy fluid is detected to fall below the desired temperature range the heater may be activated to heat the therapy fluid. If the temperature of the therapy fluid is detected to rise above the desired temperature range the cooler may be activated to cool the therapy fluid.

As non-limiting examples, controlling the temperature of the therapy fluid to attain a targeted temperature range may be implemented via mixing of via heating or cooling element.

Turning now to FIG. 1, the figure is an isometric view of an embodiment of the Thermal contrast therapy system 100 with a novel pump 144. The human interface device 102 is shown coupled to the reservoir 144 via the fluid tubing 110. The sit surface 122 located on the top of the human interface device 102 comprises the membrane 106 which expands as the therapy fluid is pumped through the membrane 106. The remote-control device 120 may be used to control the operation of the Thermal contrast therapy system 100 by communicating wirelessly with the signal receiver 140 on the human interface device 102.

Figure 2:
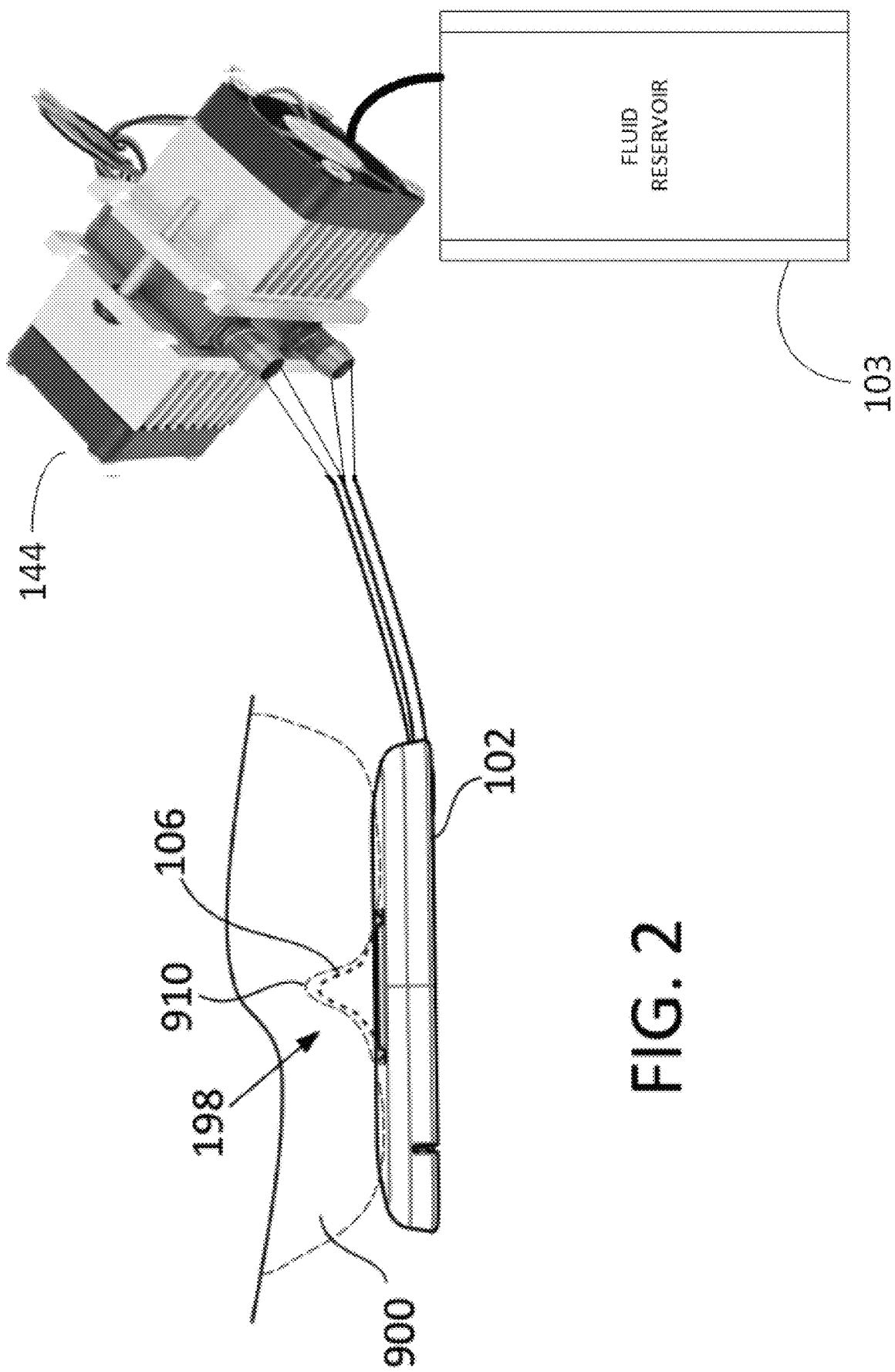
FIG. 2 is a side view illustrating an embodiment of the Thermal contrast therapy system while in use utilizing an active heating and cooling support system.

Turning now to FIG. 2, the figure is a side view illustrating an embodiment of the Thermal contrast therapy system 100 with a novel pump 144 while in use. The therapy recipient 900 is sitting upon the human interface device 102 placing the therapy site 910 above the membrane 106. The therapy fluid is flowing between the reservoir 144 and the human interface device 102 via the fluid tubing 110 and the therapy fluid has increased the pressure within the membrane 106. The membrane expansion 198 has placed the membrane 106 in contact with the therapy site 910 such that heat may flow between the therapy site 910 and the therapy fluid via the membrane 106.

Figure 3:
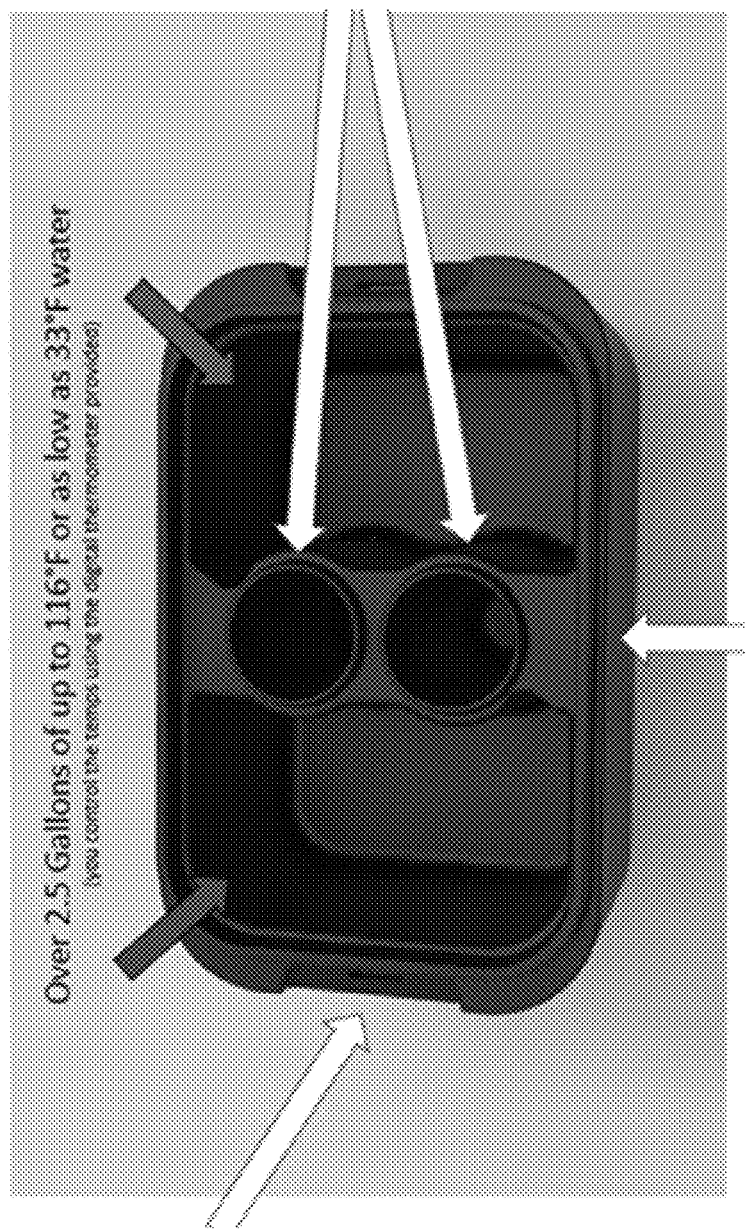
FIG. 3 is a twin tank view of the Thermal contrast therapy system showing separate thermal cavities with discrete fluid reservoirs and isolated pick-up regions.

Turning now to FIG. 3, the figure is an implementation of the true twin mode tank consistent with the embodiments of the invention.

Figure 4:
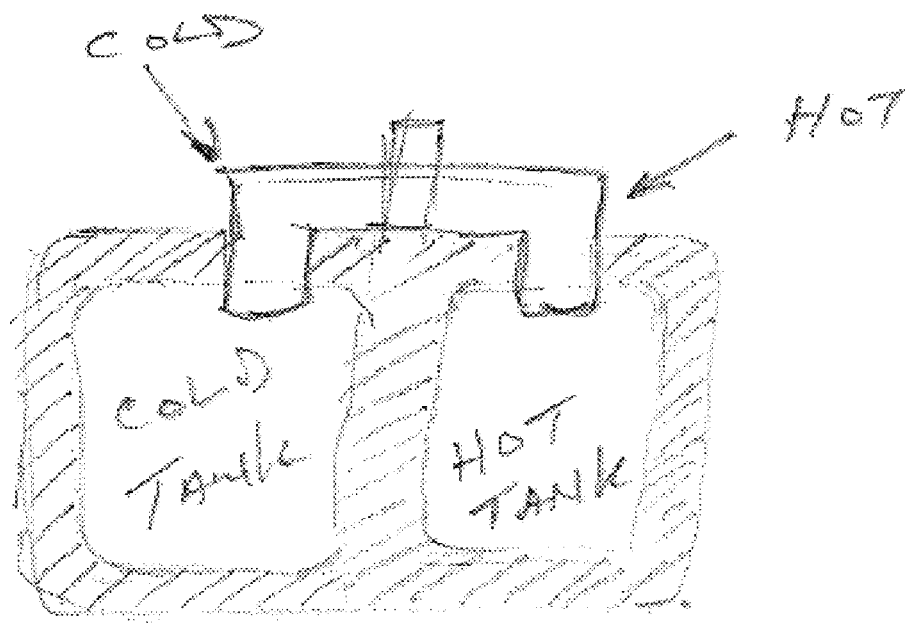
FIG. 4 is a view of the reduction of fluid volume aspect of the Thermal contrast therapy system enabled by the active heating and cooling support system.
Figure 4:
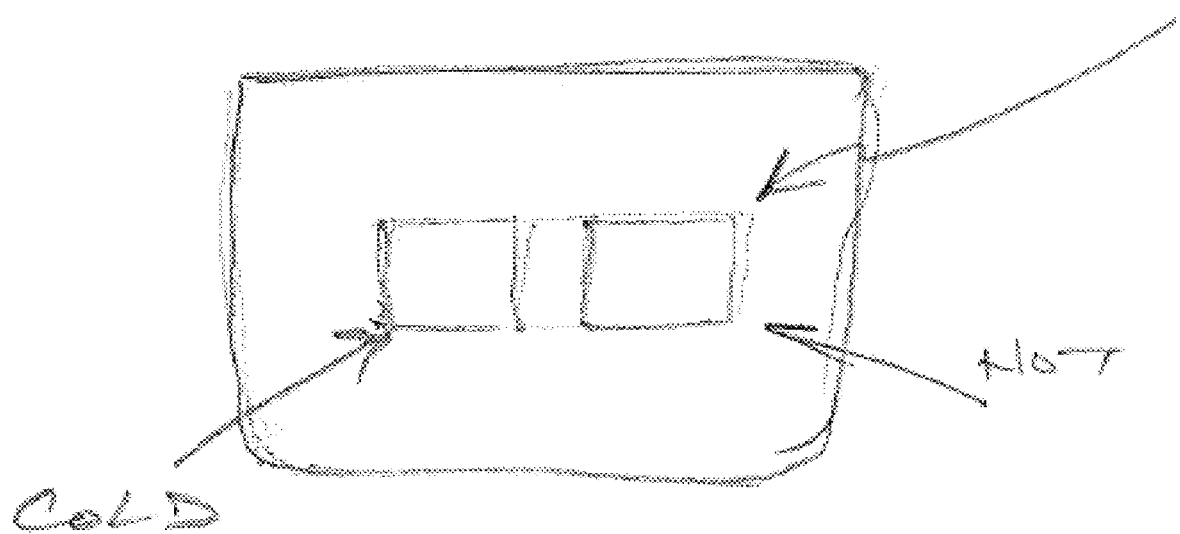

Turning now to FIG. 4, the figure is an implementation of the reduction of fluid volume aspect consistent with the embodiments of the invention. This figure presents a fluid reservoir reduction capability made possible by a thermoelectric device addition to the fluid reservoir. This reduction capability permits the device to be operated as a wearable device.

Figure 5B:
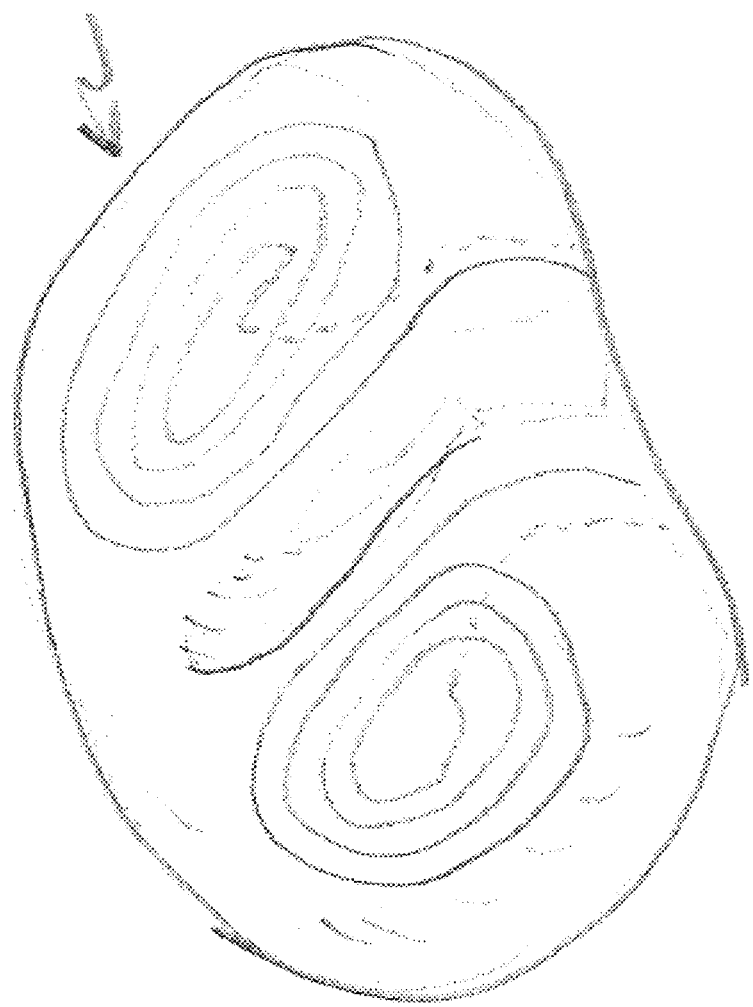
FIG. 5B is a view of the HID with fluid delivery lines delivering therapy to the buttock regions.
Figure 5A:
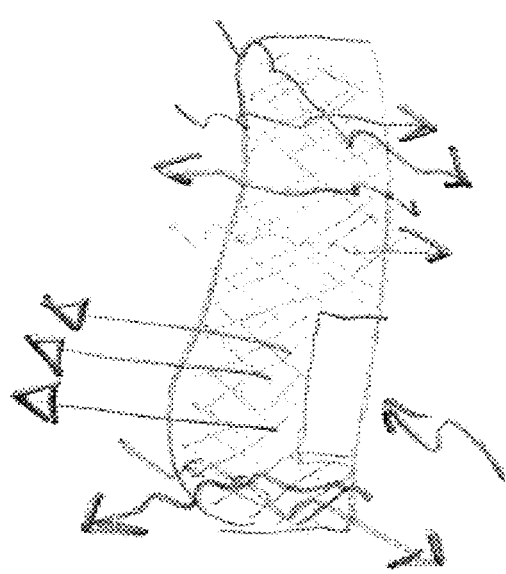
FIG. 5A is a view of the air flow aspect of the Human Interface Device (HID) element being of a lattice structure to allow air flow to therapy site(s).

Turning now to FIG. 5A, the figure is an implementation of the air flow capability consistent with the embodiments of the invention.

Turning now to FIG. 5B, the figure is a view of the HID with fluid delivery lines delivering therapy to the buttock regions.

Figure 6:
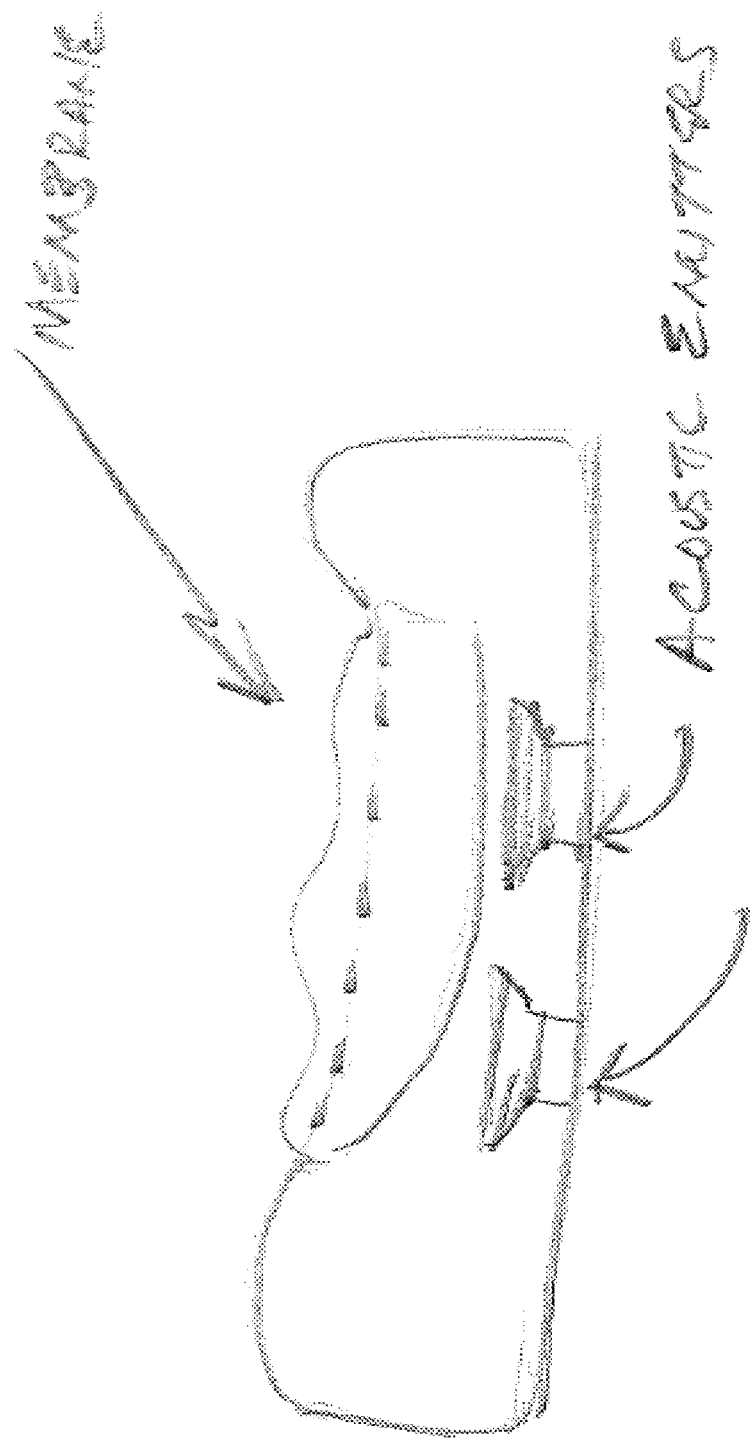
FIG. 6 is a view of the acoustic emitter aspect of the Thermal contrast therapy system.

Turning now to FIG. 6, the figure is an implementation of the acoustic emitter element consistent with the embodiments of the invention.

Figure 7:
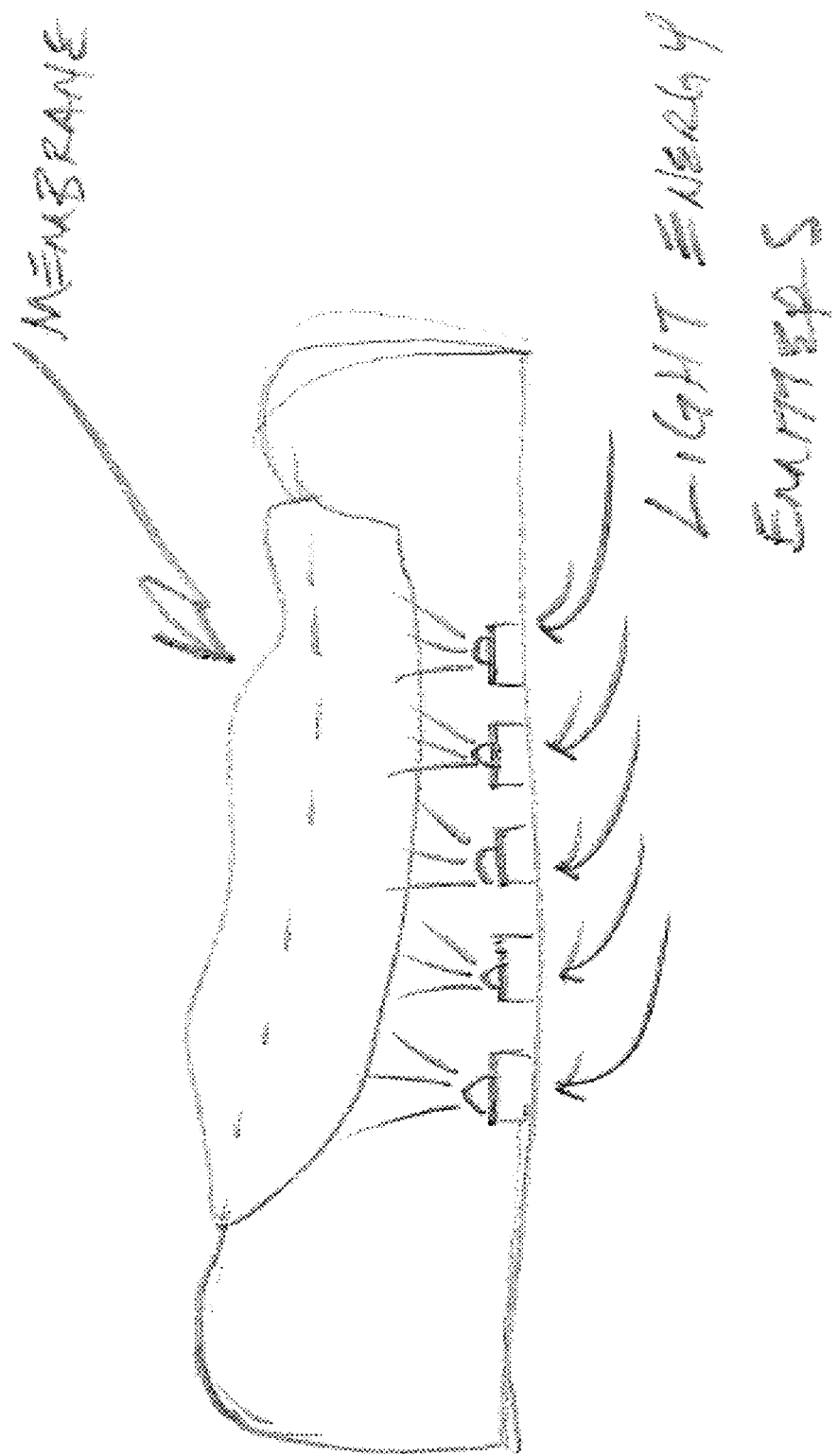
FIG. 7 is a view of the light energy emitter aspect of the Thermal contrast therapy system.

Turning now to FIG. 7, the figure is an implementation of the light energy emitter element consistent with the embodiments of the invention.

Figure 8:
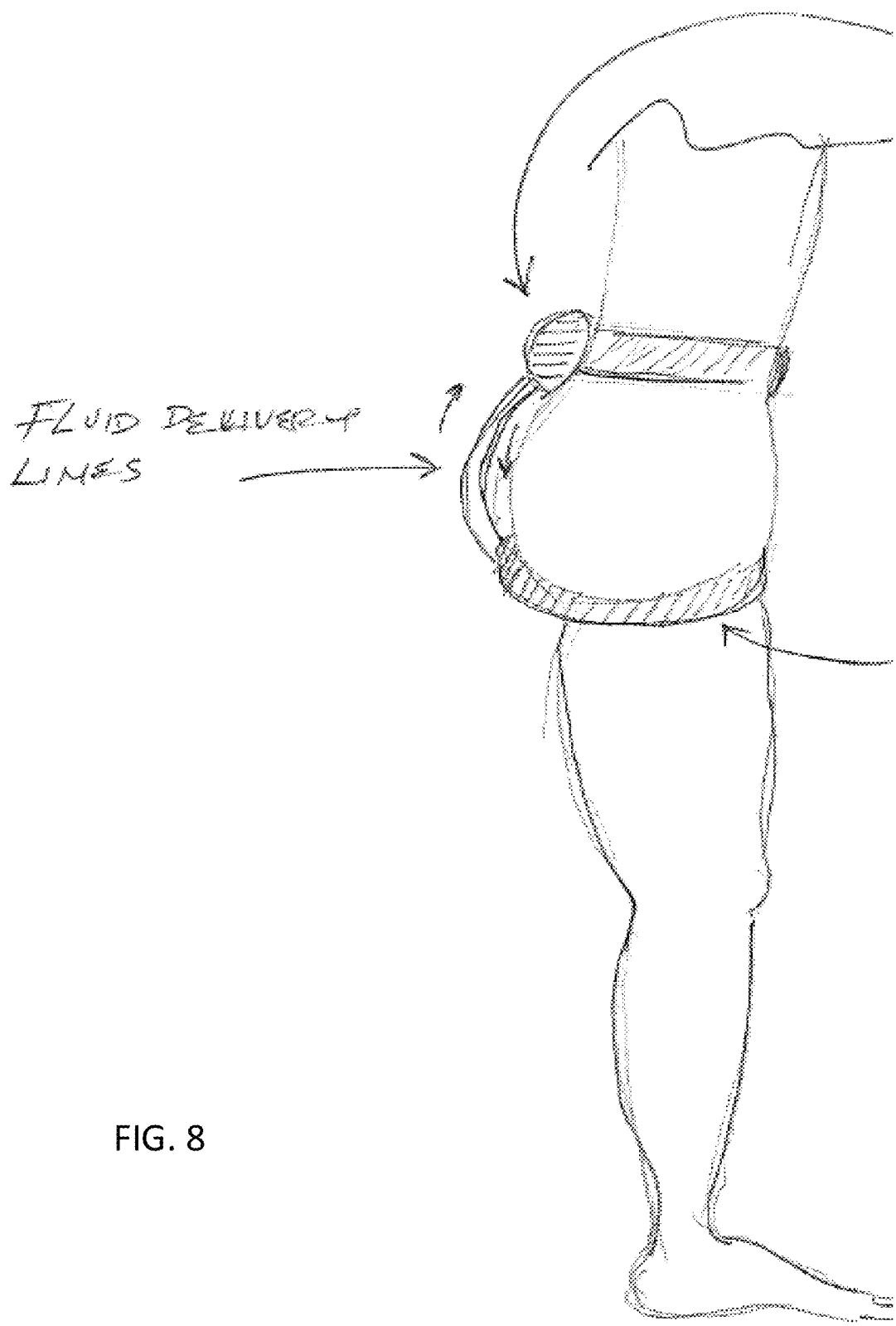
FIG. 8 is a view of the wearable/ambulatory system aspect of the Thermal contrast therapy system.

Turning now to FIG. 8, the figure is an implementation of the wearable system element consistent with the embodiments of the invention.

Figure 9:
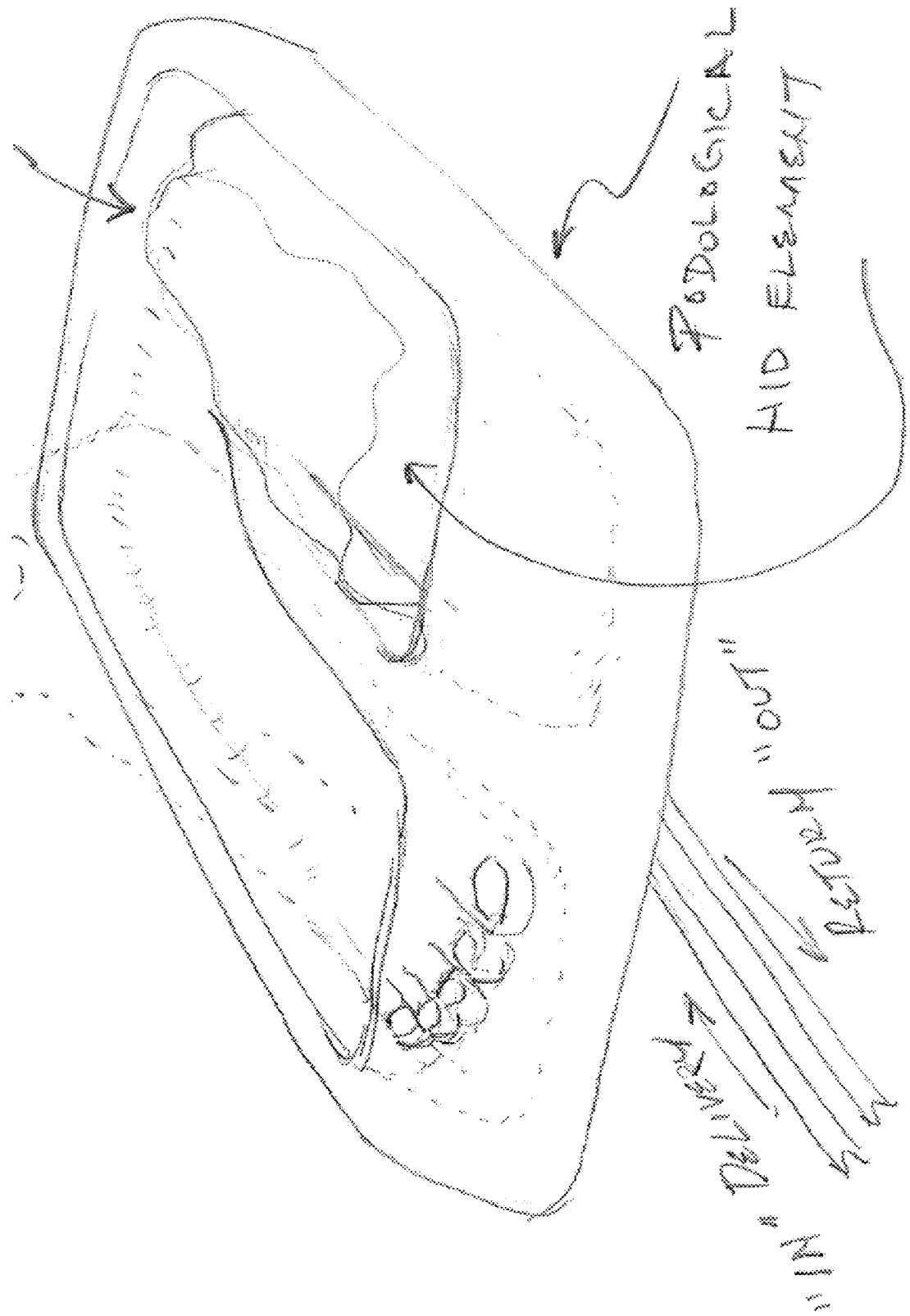
FIG. 9 is a detail view of the HID embodiment of the podological system aspect of the Thermal contrast therapy system.

Turning now to FIG. 9, the figure is an implementation of the podological system element consistent with the embodiments of the invention. The podological system element may be adapted to provide heating and cooling treatment to all distal extremities, including, without limitation, hands, fingers, feet, toes, ankles, and wrists.

Figure 10:
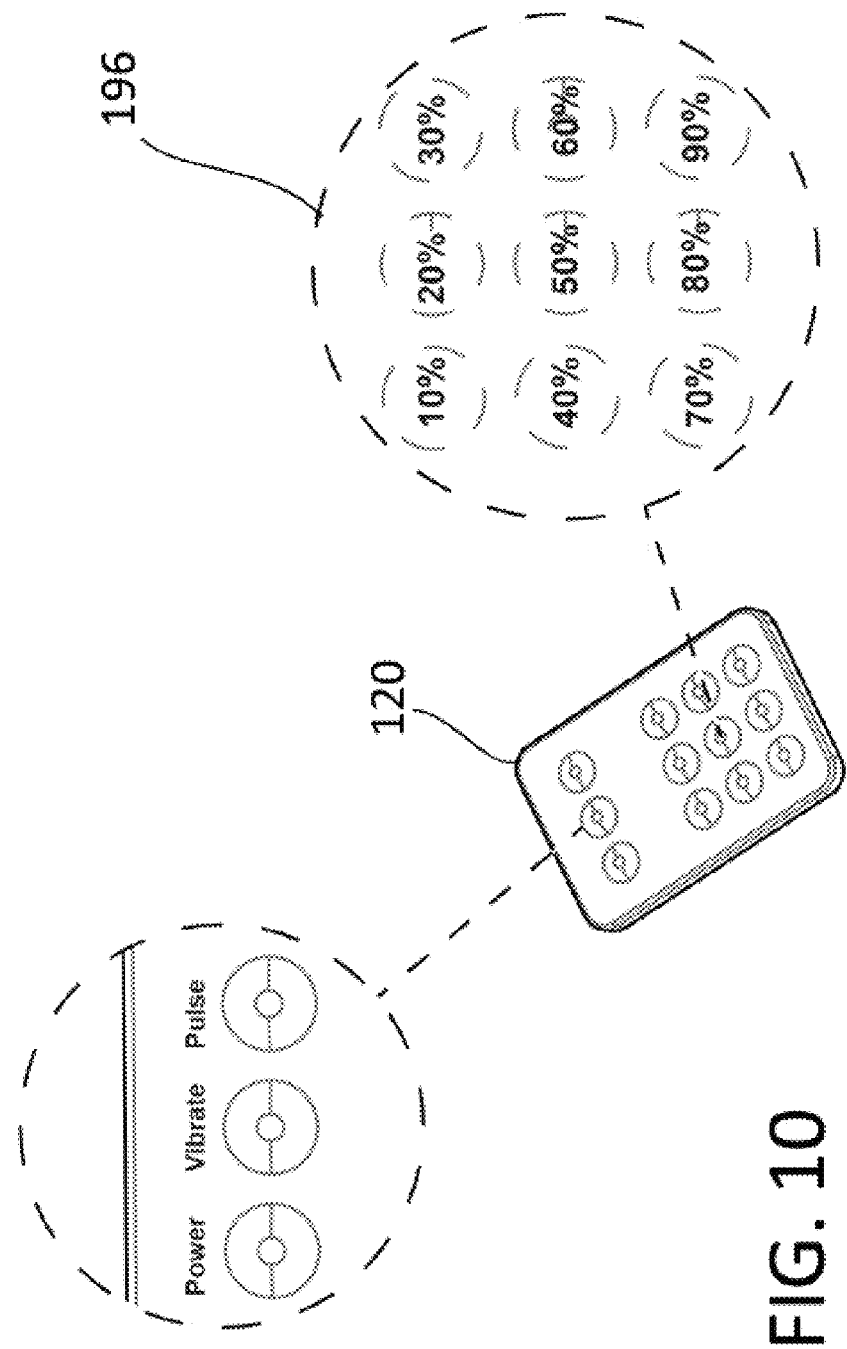
FIG. 10 is a detail view of an embodiment of the Thermal contrast therapy system illustrating the power level interface of the remote-control device.

Turning now to FIG. 10, the figure illustrates the remote-control device 120. As non-limiting examples, the remote-control device 120 may comprise the power level interface 196 for selecting the power level or other controls for establishing an on/off state or modes of operation such as vibration and pulsation. The remote-control device may be any device having a processor, memory, and a display, such as a laptop, smart phone, tablet computer, or a specialized custom interface device.

Figure 11:
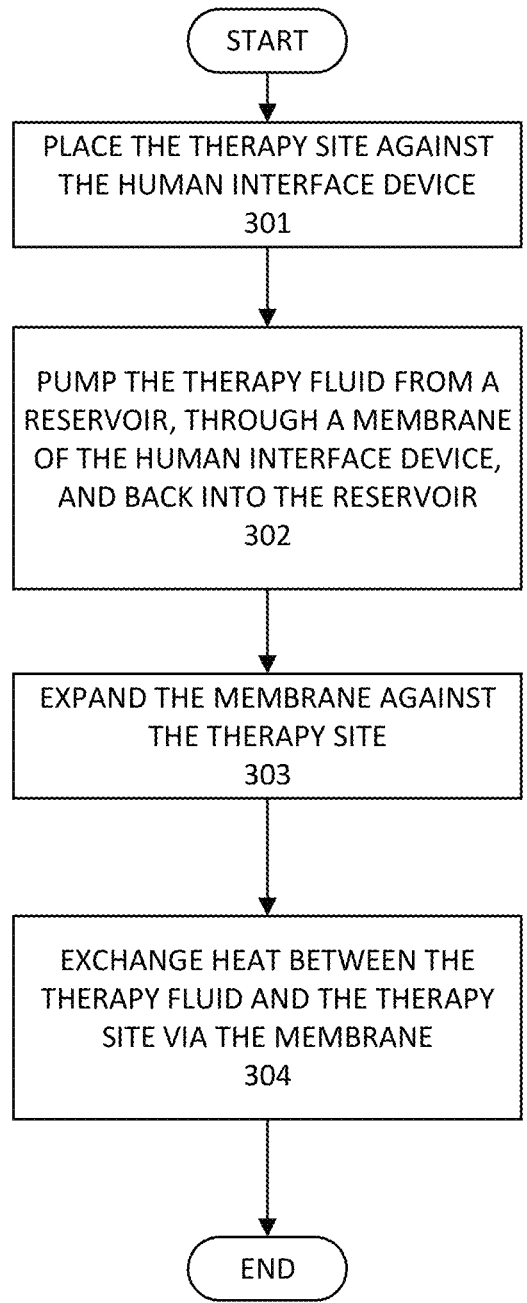
FIG. 11 is a flow diagram illustrating a method of using a Thermal contrast therapy system.

Turning now to FIG. 11, a method of using the invention is illustrated as a flow diagram. At block 301, the therapy site 910 may be placed against the human interface device 102. In some embodiments, the human interface device 102 may be placed against the therapy site 910

At block 302, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 303, the membrane 106 may expand to contact the therapy site 910 and may conform to the contour of the therapy site 910.

At block 304, heat may be exchanged between the therapy fluid and the therapy site 910 via the membrane 106. The direction and rate of the heat transfer may depend upon the relative difference in temperature between the therapy fluid and the therapy site 910. As a non-limiting example, if the therapy fluid is cooler than the therapy site 910 then heat may transfer through the membrane 106 from the therapy site 910 to the therapy fluid and may be carried away by the therapy fluid.

Figure 12:
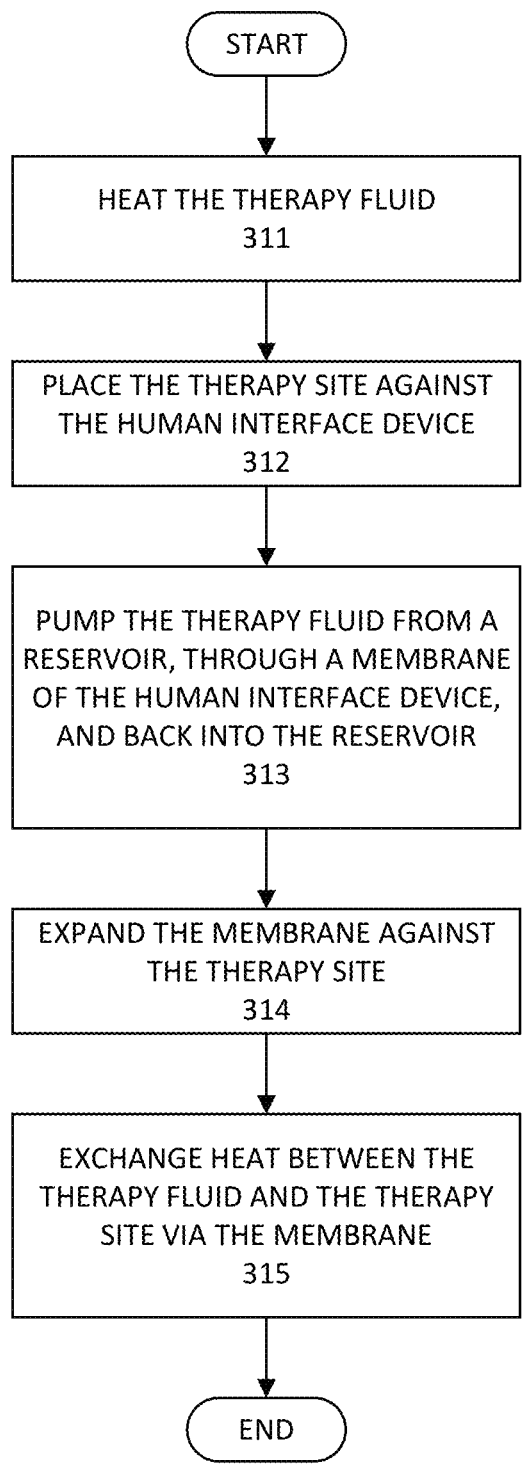
FIG. 12 is a flow diagram illustrating a method of using a Thermal contrast therapy system with pre-heated therapy fluid.

Turning now to FIG. 12, a method of using the invention with heated fluid is illustrated as a flow diagram. At block 311, the therapy fluid may be heated. As non-limiting examples, the therapy fluid may be heated by the heater within the Thermal contrast therapy system 100 or the therapy fluid may be heated as a separate operation before placing the therapy fluid into the reservoir 144.

At block 312, the therapy site 910 may be placed against the human interface device 102. In some embodiments, the human interface device 102 may be placed against the therapy site 910

At block 313, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 314, the membrane 106 may expand to contact the therapy site 910 and may conform to the contour of the therapy site 910.

At block 315, heat may be exchanged between the therapy fluid and the therapy site 910 via the membrane 106. Because the therapy fluid has been heated to a temperature that may be warmer than the temperature of the therapy site 910, the heat may be expected to flow from the therapy fluid to the therapy site 910 via the membrane 106.

Figure 13:
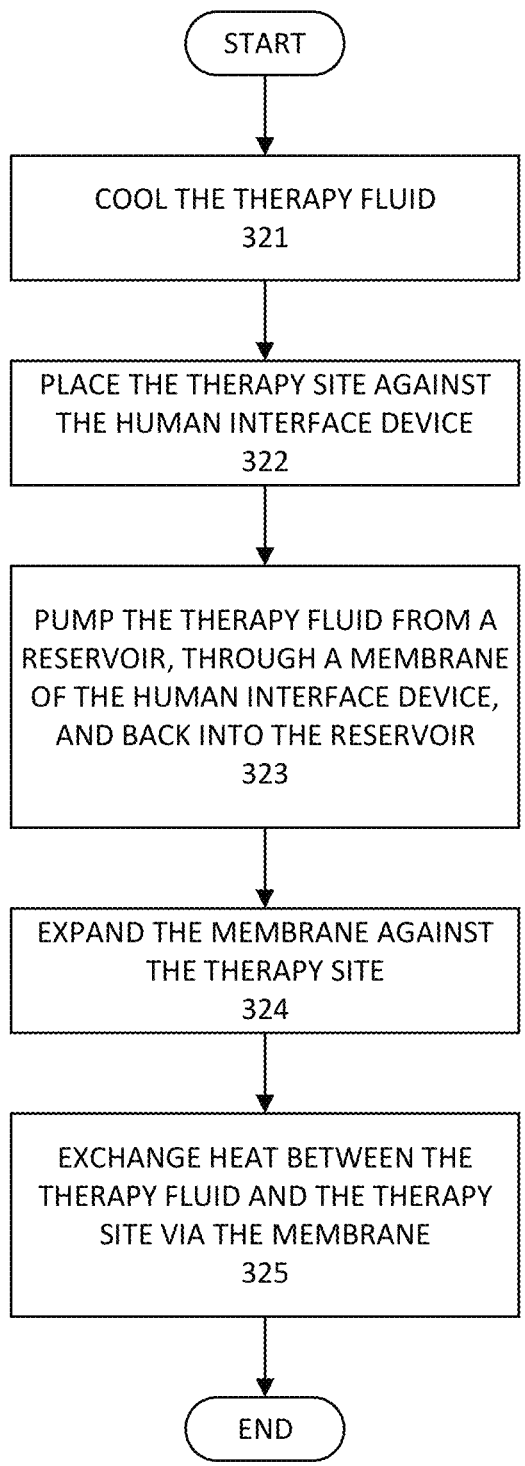
FIG. 13 is a flow diagram illustrating a method of using a Thermal contrast therapy system with pre-cooled therapy fluid.

Turning now to FIG. 13, a method of using the invention with cooled fluid is illustrated as a flow diagram. At block 321, the therapy fluid may be cooled. As non-limiting examples, the therapy fluid may be cooled by the cooler within the Thermal contrast therapy system 100 or the therapy fluid may be cooled as a separate operation before placing the therapy fluid into the reservoir 144.

At block 322, the therapy site 910 may be placed against the human interface device 102. In some embodiments, the human interface device 102 may be placed against the therapy site 910

At block 323, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 324, the membrane 106 may expand to contact the therapy site 910 and may conform to the contour of the therapy site 910.

At block 325, heat may be exchanged between the therapy fluid and the therapy site 910 via the membrane 106. Because the therapy fluid has been cooled to a temperature that may be cooler than the temperature of the therapy site 910, the heat may be expected to flow from the therapy site 910 to the therapy fluid via the membrane 106.

Figure 14:
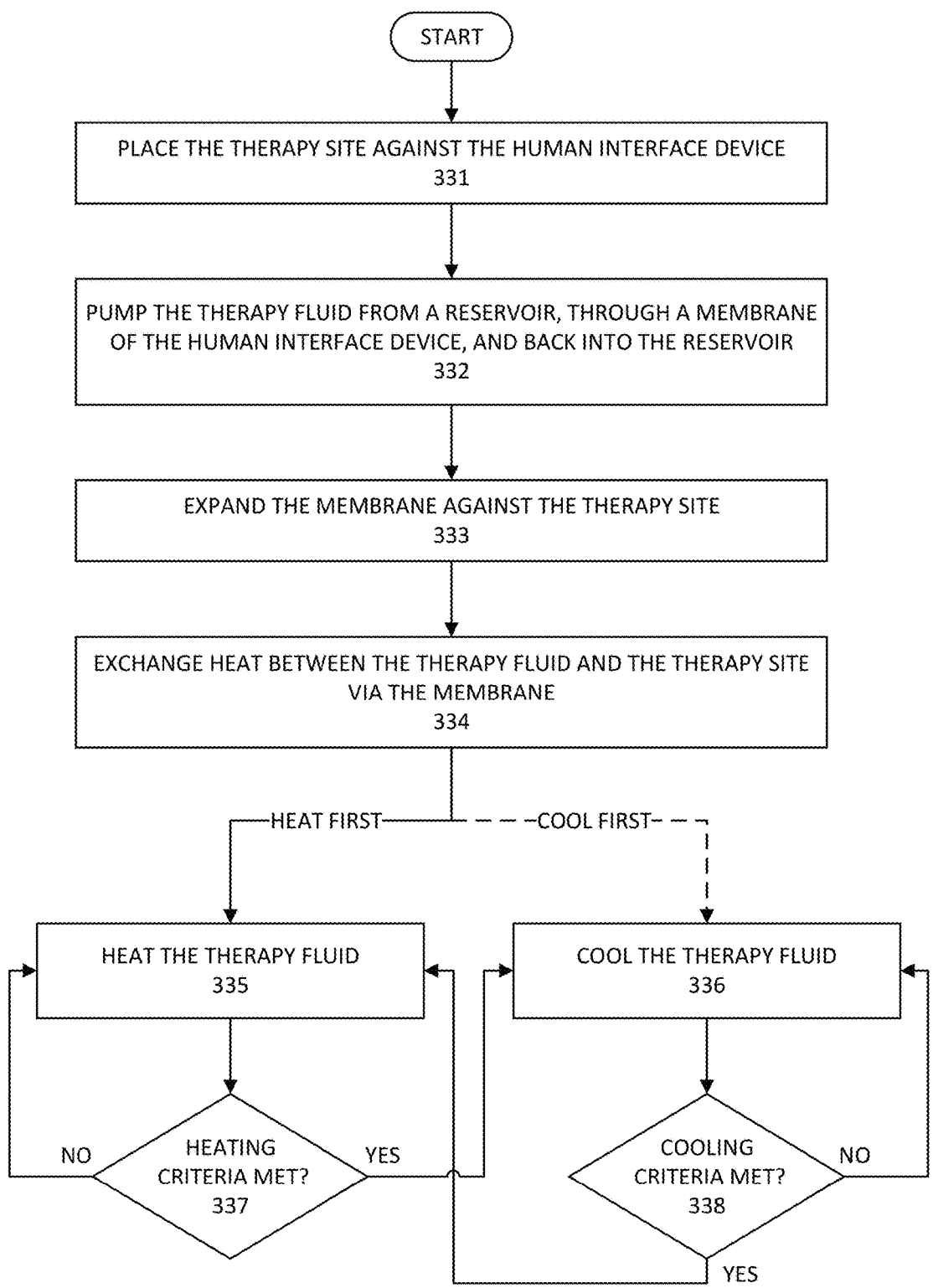
FIG. 14 is a flow diagram illustrating a method of using a Thermal contrast therapy system with therapy fluid that is alternately heated and cooled.

Turning now to FIG. 14, a method of using the invention while alternately heating and cooling the fluid is illustrated as a flow diagram. At block 331, the therapy site 910 may be placed against the human interface device 102. In some embodiments, the human interface device 102 may be placed against the therapy site 910

At block 332, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 333, the membrane 106 may expand to contact the therapy site 910 and may conform to the contour of the therapy site 910.

At block 334, heat may be exchanged between the therapy fluid and the therapy site 910 via the membrane 106. The direction and rate of the heat transfer may depend upon the relative difference in temperature between the therapy fluid and the therapy site 910. As a non-limiting example, if the therapy fluid is cooler than the therapy site 910 then heat may transfer through the membrane 106 from the therapy site 910 to the therapy fluid and may be carried away by the therapy fluid.

Exiting block 334, the Thermal contrast therapy system 100 may heat the therapy fluid first or may cool the therapy fluid first. As non-limiting examples, the decision to heat first or to cool first may be preprogrammed into the Thermal contrast therapy system 100, may be made randomly, or may be selected by the therapy recipient 900. In FIG. 14, the path marked HEAT FIRST shows a decision to heat first while the path marked COOL FIRST shows a decision to cool first.

At block 335, the therapy fluid may be heated. As non-limiting examples, the therapy fluid may be heated by the heater within the Thermal contrast therapy system 100 or the therapy fluid may be heated using one or more valves to select a heated water reservoir as a source of the therapy fluid.

At block 337, the Thermal contrast therapy system 100 may determine whether a heating criterion has been met. As non-limiting examples, the heating criteria may be based upon reaching a specific threshold temperature or range of temperatures, may be timed, or combinations thereof. If the heating criteria has not been met, the NO exit from block 337 may return to block 335 to continue heating the therapy fluid. If the heating criteria has been met, the YES exit from block 337 may branch to block 336 to begin cooling the therapy fluid.

At block 336, the therapy fluid may be cooled. As non-limiting examples, the therapy fluid may be cooled by the cooler within the Thermal contrast therapy system 100 or the therapy fluid may be cooled using one or more valves to select a cooled water reservoir as a source of the therapy fluid.

At block 338, the Thermal contrast therapy system 100 may determine whether a cooling criterion has been met. As non-limiting examples, the cooling criteria may be based upon reaching a specific threshold temperature or range of temperatures, may be timed, or combinations thereof. If the cooling criteria has not been met, the NO exit from block 338 may return to block 336 to continue cooling the therapy fluid. If the cooling criteria has been met, the YES exit from block 338 may branch to block 335 to begin heating the therapy fluid.

The method may alternate between heating and cooling the therapy fluid until the Thermal contrast therapy system 100 is turned off or until another mode of operation is selected.

Figure 15:
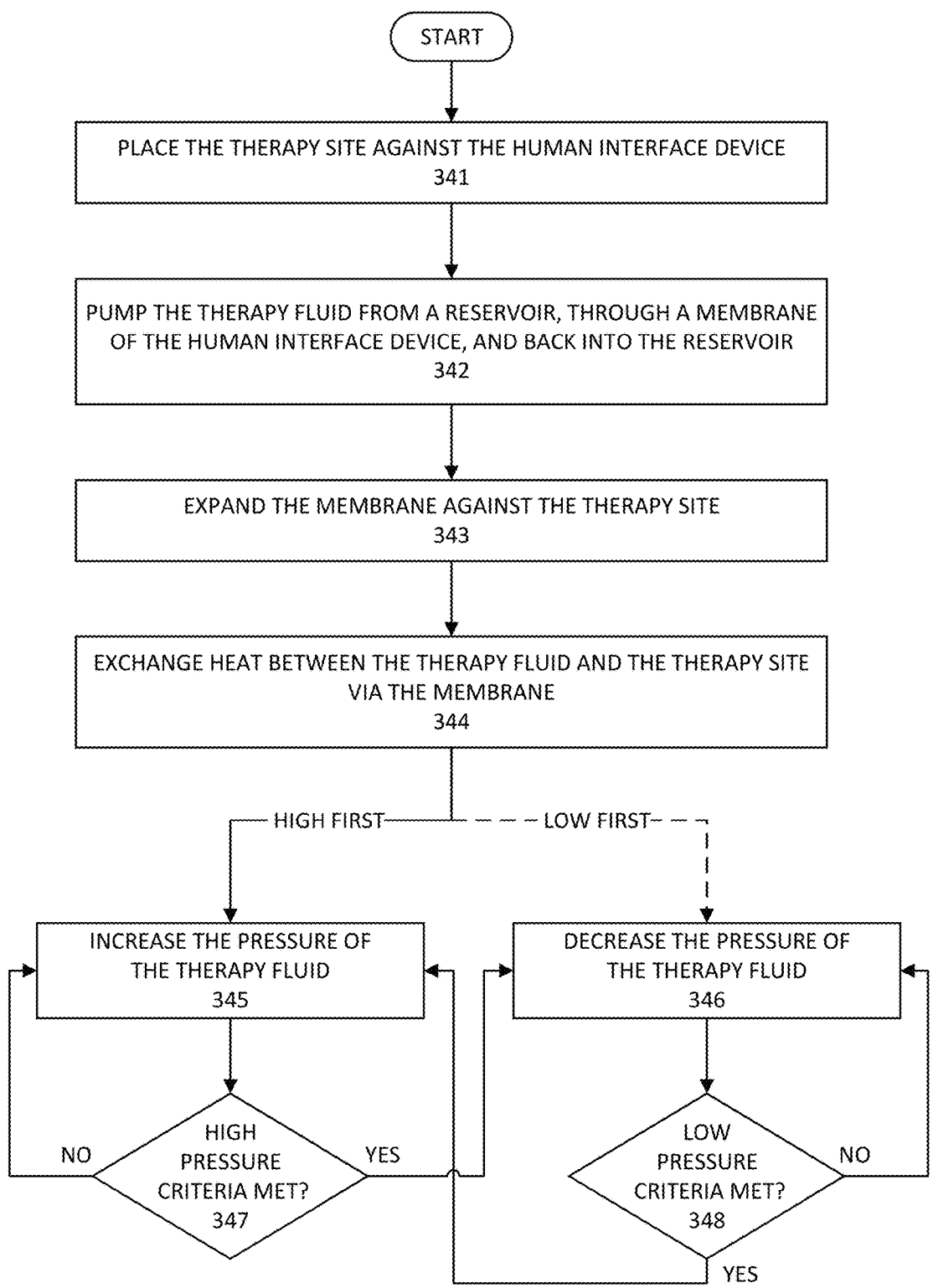
FIG. 15 is a flow diagram illustrating a method of using a Thermal contrast therapy system while varying the pressure of the therapy fluid.

Turning now to FIG. 15, a method of using the invention while varying the pressure of the fluid is illustrated as a flow diagram. At block 341, the therapy site 910 may be placed against the human interface device 102. In some embodiments, the human interface device 102 may be placed against the therapy site 910

At block 342, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 343, the membrane 106 may expand to contact the therapy site 910 and may conform to the contour of the therapy site 910.

At block 344, heat may be exchanged between the therapy fluid and the therapy site 910 via the membrane 106. The direction and rate of the heat transfer may depend upon the relative difference in temperature between the therapy fluid and the therapy site 910. As a non-limiting example, if the therapy fluid is cooler than the therapy site 910 then heat may transfer through the membrane 106 from the therapy site 910 to the therapy fluid and may be carried away by the therapy fluid.

Exiting block 344, the Thermal contrast therapy system 100 may increase the pressure of the therapy fluid first or may decrease the pressure of the therapy fluid first. As non-limiting examples, the decision to increase the pressure first or to decrease the pressure first may be preprogrammed into the Thermal contrast therapy system 100, may be made randomly, or may be selected by the therapy recipient 900. In FIG. 15, the path marked HIGH FIRST shows a decision to increase the pressure first while the path marked LOW FIRST shows a decision to lower the pressure first.

At block 345, the pressure of the therapy fluid may be increased. As a non-limiting example, the pressure of the therapy fluid may be increased by increasing the power level of the power supply 118 that energizes the pump 116. As non-limiting examples, the power level increase may be initiated by the Thermal contrast therapy system 100 or by the therapy recipient 900 using the remote-control device 120.

At block 347, the Thermal contrast therapy system 100 may determine whether a high-pressure criterion has been met. As non-limiting examples, the high-pressure criteria may be based upon reaching a specific threshold pressure or range of pressures, may be timed, may be determined by the therapy recipient 900, or combinations thereof. If the high-pressure criteria have not been met, the NO exit from block 347 may return to block 345. If the high-pressure criteria have been met, the YES exit from block 347 may branch to block 346 to begin decreasing the pressure of the therapy fluid.

At block 346, the pressure of the therapy fluid may be decreased. As a non-limiting example, the pressure of the therapy fluid may be decreased by decreasing the power level of the power supply 118 that energizes the pump 116. As non-limiting examples, the power level decrease may be initiated by the Thermal contrast therapy system 100 or by the therapy recipient 900 using the remote-control device 120.

At block 348, the Thermal contrast therapy system 100 may determine whether a low-pressure criterion has been met. As non-limiting examples, the low-pressure criteria may be based upon reaching a specific threshold pressure or range of pressures, may be timed, may be determined by the therapy recipient 900, or combinations thereof. If the low-pressure criteria have not been met, the NO exit from block 348 may return to block 346. If the low-pressure criteria have been met, the YES exit from block 348 may branch to block 345 to begin increasing the pressure of the therapy fluid.

The method may alternate between increasing and decreasing the pressure of the therapy fluid until the Thermal contrast therapy system 100 is turned off or until another mode of operation is selected.

Figure 16:
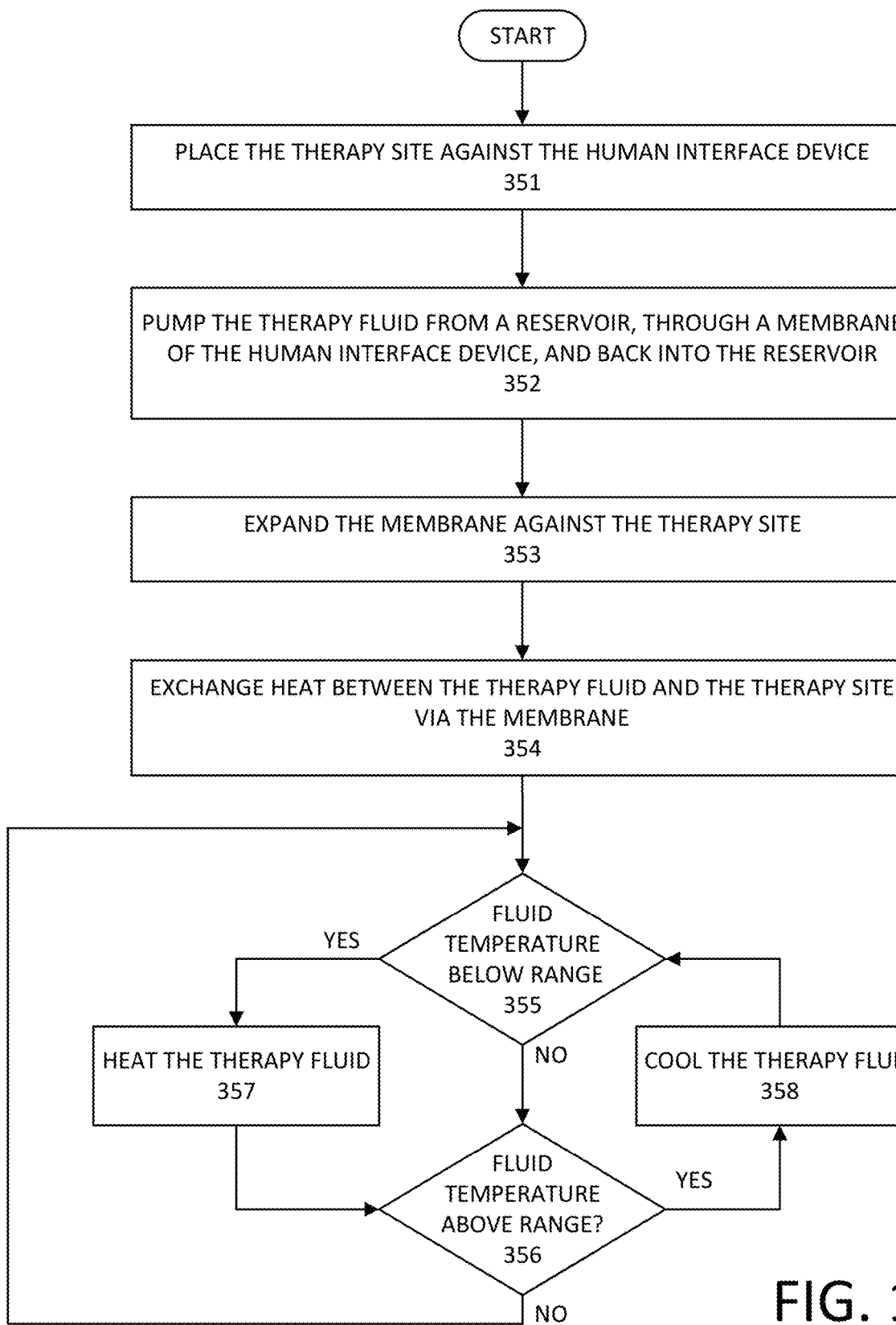
FIG. 16 is a flow diagram illustrating a method of using a Thermal contrast therapy system while monitoring and controlling the temperature of the therapy fluid.

Turning now to FIG. 16, a method of using the invention while monitoring and controlling the temperature is illustrated as a flow diagram. At block 351, the therapy site 910 may be placed against the human interface device 102. In some embodiments, the human interface device 102 may be placed against the therapy site 910

At block 352, the therapy fluid may be pumped out of the reservoir 144, through the membrane 106, and back to the reservoir 144. In some embodiments, the therapy fluid may be pumped into a different reservoir than the reservoir that sourced the therapy fluid.

At block 353, the membrane 106 may expand to contact the therapy site 910 and may conform to the contour of the therapy site 910.

At block 354, heat may be exchanged between the therapy fluid and the therapy site 910 via the membrane 106. The direction and rate of the heat transfer may depend upon the relative difference in temperature between the therapy fluid and the therapy site 910. As a non-limiting example, if the therapy fluid is cooler than the therapy site 910 then heat may transfer through the membrane 106 from the therapy site 910 to the therapy fluid and may be carried away by the therapy fluid.

At block 355, the Thermal contrast therapy system 100 may determine whether the temperature of the therapy fluid is below a predetermined range of temperatures. If the temperature of the therapy fluid is not below the range, the NO exit from block 355 may continue to block 356. If the temperature of the therapy fluid is below the range, the YES exit from block 355 may branch to block 357.

At block 357, the therapy fluid may be heated. As non-limiting examples, the therapy fluid may be heated by the heater within the Thermal contrast therapy system 100 or the therapy fluid may be heated using one or more valves to select a heated water reservoir as a source of the therapy fluid.

At block 356, the Thermal contrast therapy system 100 may determine whether the temperature of the therapy fluid is above a predetermined range of temperatures. If the temperature of the therapy fluid is not above the range, the NO exit from block 356 may continue to block 355. If the temperature of the therapy fluid is above the range, the YES exit from block 356 may branch to block 358.

At block 358, the therapy fluid may be cooled. As non-limiting examples, the therapy fluid may be cooled by the cooler within the Thermal contrast therapy system 100 or the therapy fluid may be cooled using one or more valves to select a cooled water reservoir as a source of the therapy fluid.

While certain illustrative embodiments have been described, it is evident that many alternatives, modifications, permutations and variations will become apparent to those skilled in the art in light of the foregoing description.

What is claimed is:

1. A system for providing Thermal contrast therapy comprising
    a human adapted therapy device comprising a fluid membrane barrier, a human interface device (HID) further comprising a seat, fluid tubing, a pump, and a reservoir;
    where the HID seat further comprises a surface contact membrane that is adapted to contact an external surface of the anatomy of a therapy recipient comprising an exterior posterior therapy site;
    where a therapy fluid or gel is configured to be pumped by a pump from the reservoir to the HID and back to the reservoir via the fluid tubing;
    where the therapy fluid exerts pressure to increase contact with said external surface of a therapy recipient through the expansion of said surface contact membrane of the HID;
    said HID seat surface contact membrane having one or more flexible lattice elements further comprising channel structures for movement of said therapy fluid or gel through said HID seat and replaceable lattice pods to permit airflow through said HID seat when said HID seat is in contact with said external posterior therapy site;
    where the surface contact membrane is adapted to conform to the contours of said external posterior therapy site on the therapy recipient;
    where a transfer of energy is configured to be exchanged between the external posterior therapy site and the therapy fluid or gel via the surface contact membrane of said HID seat.

2. The system according to claim 1
    where heated therapy fluid in the reservoir is configured to be pumped through the surface contact membrane of the HID.

3. The system according to claim 1
    where cooled therapy fluid in the reservoir is configured to be pumped through the surface contact membrane of the HID.

4. The system according to claim 1 where alternately heated and cooled therapy fluid in the reservoir is configured to be pumped through the surface contact membrane of the HID.

5. The system according to claim 1 where the reservoir is insulated to maintain the temperature of the therapy fluid.

6. The system according to claim 1
where a power supply power the pump;
where a power level of the power supply to the pump motor determines the flow rate of the therapy fluid and the pressure within the membrane.

7. The system according to claim 1 where the reservoir decouple from the fluid tubing by disconnecting a pair of self-sealing couplers located on the fluid tubing from bulkhead ports on a reservoir lid of the reservoir.

8. The system according to claim 1
where the surface membrane expands as pressure within the surface membrane increases;
where the surface membrane contracts as pressure within the surface membrane decreases.

9. The system according to claim 1
where a remote-control device is operable to wirelessly control the HID remotely;
where the remote-control device is adapted to provide a power level interface to an operator;
where the remote-control device communicates a power level selection made on the HID through a signal sent from the remote-control device to a signal receiver located on the HID;
where the power supply is operable to change the power level of the pump responsive to the signal sent from the remote-control device.

10. The system according to claim 9 where the remote-control device is any of a laptop, tablet, smart phone, custom designed device, or handheld controller.

11. A method for providing thermal contrast therapy comprising
placing an external therapy site comprising an external posterior surface of the anatomy of a therapy recipient against a surface contact membrane of a human interface device (HID) seat portion;
pumping a therapy fluid or gel from a reservoir, through said surface contact membrane in external surface contact with said therapy site;
where said surface contact membrane further comprises a membrane and one or more lattice elements having channel structures for movement of said therapy fluid or gel through the HID seat portion, and back into the reservoir and replaceable lattice pods to permit airflow when said HID seat portion is in contact with said external posterior therapy site;
further conforming said HID seat portion surface contact membrane with said external posterior therapy site by exerting pressure from said pumping of the therapy fluid to expand the surface contact membrane against the external therapy site; and,
exchanging heat between the therapy fluid or gel and the external posterior therapy site via the HID seat portion surface contact membrane.

12. The method according to claim 11 further comprising; heating the therapy fluid before pumping the therapy fluid through the HID seat.

13. The method according to claim 12 further comprising; heating the therapy fluid to a temperature in the range of 100 to 118 degrees Fahrenheit.

14. The method according to claim 11 further comprising cooling the therapy fluid before pumping the therapy fluid through the HID seat.

15. The method according to claim 14 further comprising cooling the therapy fluid to a temperature in the range of 32.5 to 70 degrees Fahrenheit.

16. The method according to claim 11 further comprising alternately heating and cooling the therapy fluid such that the temperature of the therapy fluid fluctuates above and below an internal body temperature of a therapy recipient.

17. The method according to claim 11 further comprising varying the pressure of the therapy fluid or gel as the therapy fluid or gel flows through the membrane.

18. The method according to claim 11 further comprising monitoring the temperature of the therapy fluid or gel and controlling the temperature of the therapy fluid or gel to attain a pre-configured targeted temperature range.

* * * * *